(12) United States Patent
Natsch et al.

(10) Patent No.: US 7,264,956 B2
(45) Date of Patent: Sep. 4, 2007

(54) COMPOUNDS AND METHODS FOR INHIBITING AXILLARY MALODOUR

(75) Inventors: Andreas Natsch, Uetikon (CH); Gonzalo Acuna, Dietlikon (CH); Marie-Claude Fournie-Zaluski, Paris (FR); Hans Gfeller, Aathal-Seegräben (CH)

(73) Assignee: Givaudan SA, Vernier (CH)

( * ) Notice: Subject to any disclaimer, the term of this patent is extended or adjusted under 35 U.S.C. 154(b) by 0 days.

(21) Appl. No.: 10/477,858

(22) PCT Filed: May 14, 2002

(86) PCT No.: PCT/CH02/00262

§ 371 (c)(1),
(2), (4) Date: Jun. 17, 2004

(87) PCT Pub. No.: WO02/092024

PCT Pub. Date: Nov. 21, 2002

(65) Prior Publication Data

US 2004/0241795 A1 Dec. 2, 2004

(30) Foreign Application Priority Data

May 14, 2001 (EP) .................... 01111637

(51) Int. Cl.
C12N 9/00 (2006.01)
C12N 9/78 (2006.01)
C12N 15/70 (2006.01)
C12N 5/16 (2006.01)
C12P 21/06 (2006.01)
C07H 21/04 (2006.01)

(52) U.S. Cl. ............... 435/227; 435/183; 435/69.1; 435/320.1; 435/325; 536/23.2

(58) Field of Classification Search ............... 435/183, 435/227; 536/23.2
See application file for complete search history.

(56) References Cited

U.S. PATENT DOCUMENTS 3,934,004 A 1/1976 Orren
4,745,067 A 5/1988 Umezawa et al. .......... 435/228
5,676,937 A 10/1997 Eigen et al.

FOREIGN PATENT DOCUMENTS

| DE | 198 55 956 A1 | 6/2000 |
|---|---|---|
| DE | 198 58 811 A1 | 6/2000 |
| EP | 0 815 833 A2 | 1/1998 |
| EP | 1 258 531 A1 | 11/2002 |
| JP | 2000288076 | 10/2000 |
| WO | WO98/27201 | 7/1998 |
| WO | WO98/56342 | 12/1998 |
| WO | WO 00/01355 | 1/2000 |
| WO | WO 00/01356 | 1/2000 |

OTHER PUBLICATIONS

Birnbaum et al. "Specificity of amino acid acylases", J. Biol. Chem. 194: 455-470, 1952.*
Pittelkow et al. "Human and porcine aminoacylase I overproduced in a Baculovirus expression vector system: Evidence for structural and functional identity with enzymes isolated from kidney", Protein Expression and Purification 12: 269-276, 1998.*
PCT International Search Report, dated Aug. 14, 2002, for PCT/CH02/00262.
Natsch et al. "A Specific Bacterial Aminoacylase Cleaves Odorant Precursors Secreted in the Human Axilla".
Pittelkow et al. "Human and Porcine Aminoacylase I Overproduced in a Baculovirus Expression Vector System: Evidence for Structural and Functional Identity with Enzymes Isolated from Kidney".
Gower et al. Comparison of 16-Androstene Steroid Concentrations in Sterile Apocrine Sweat and Axillary Secretions: Interconversions of 16-Androstenes by the Axillary Microflora-a Mechanism for Axillary Odour Production in Man?.
Database EMBL "Online!" May 1, 2001, Database accession No. Q9REM4, XP002233278.
Froebe et al. "Axillary malodor production: A new mechanism".
Zeng et al. "Analysis of Characteristics Odors from Human Male Axillae".
Bardonnet, N. et al. "Improved vactors for transcriptional signal screening in corynebacteria", FEMS Microbiology Letters 84 (1991) 97-102.
Fischer, Emil et al. Synthesis of polypeptides- (XXII) derives. Of 1-phenylalanine, Organic Chemistry, pp. 813-814.
Labows et al., "Axillary Odor, Determination, Formation, and Control", Cosmet. Sci Technol. Ser. (1999), 20:59-82.
Schmitt, M.P. "Transcription of the Corynebacterium diphtheriae hmuO Gene is Regulated by Iron and Heme", Infection and Immunity, 1997, 65(11):4634-4641.
Boyd, Andrew E. "Synthesis of Alkyl Phosphinic Acids from Silyl Phosphonites and Alkyl Halides", Tetrahedron Letters, 1994, 24, 4223-4226.
Prabhu, K.R. et al. "Unprecedented Selective Aminolysis: Aminopropyl Phosphine as a Building Block for a New Family of Air Stable Mono-, Bis-, and Tris-Primary Phosphines", J. Am. Chem. Soc. 2000, 122, 1554-1555.
Haynes, R.K. et al. "Diastere- and Regioselectivity in the Reactions of Dilithiated Allylic Secondary Amides with Cyclopent-2-enone", J. Org. Chem, 1995, 60, 4690-4691.

\* cited by examiner

Primary Examiner—Manjunath N. Rao
Assistant Examiner—Iqbal Chowdhury
(74) Attorney, Agent, or Firm—Norris McLaughlin & Marcus, PA

(57) ABSTRACT

Enzymes mediating in the release of compounds characteristic of human malodour and in particular axillary malodour, and compounds that inhibit said enzymes having the general formula (I)

$$R_1-X-Y-\underset{CONH_2}{\overset{COOH}{\diagup}}$$

I

4 Claims, 3 Drawing Sheets

Scheme 3

COMPOUNDS AND METHODS FOR INHIBITING AXILLARY MALODOUR

Figure 1:
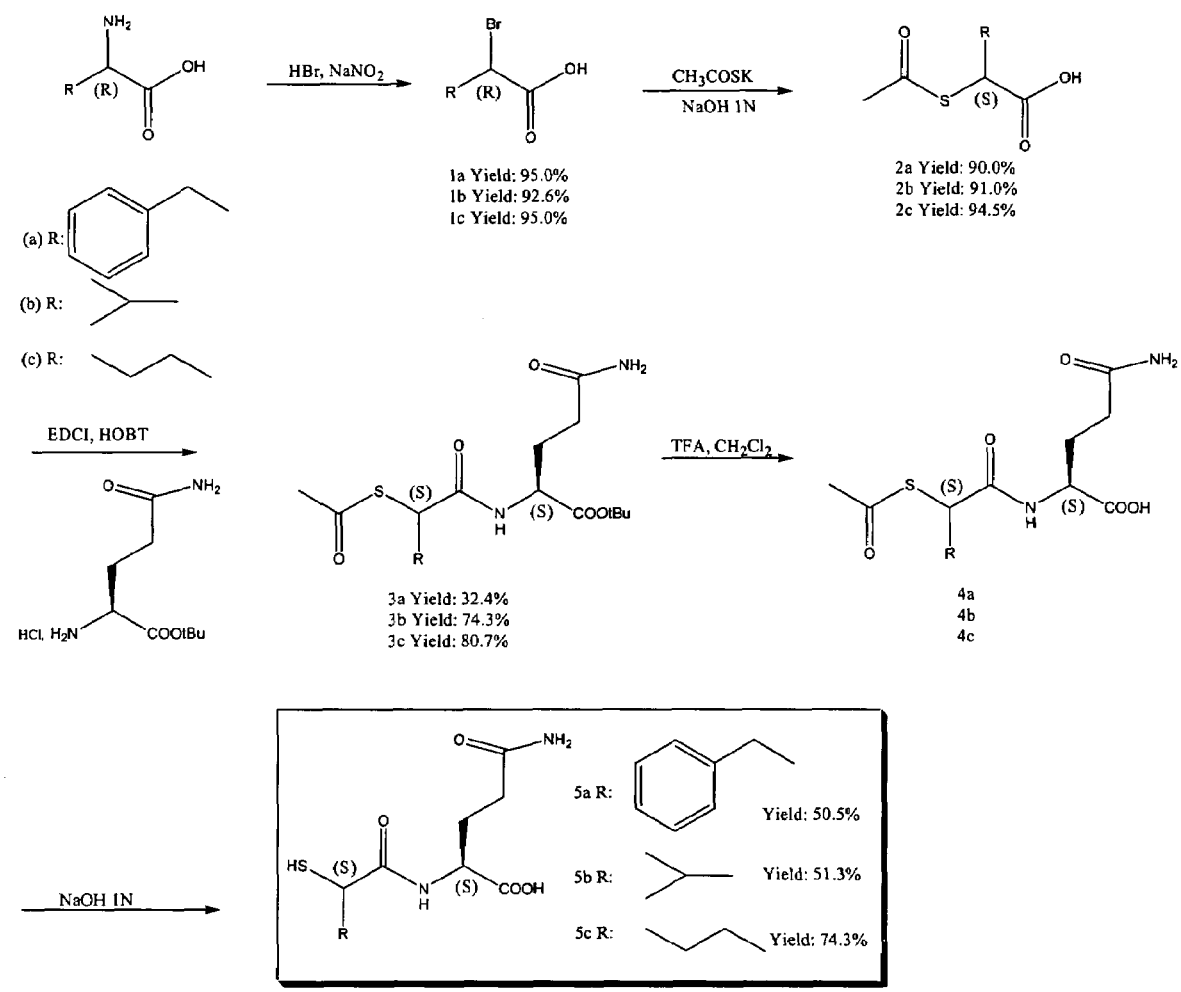

This invention is concerned with methods, compounds and compositions useful for the prevention or suppression of human malodour, in particular human axillary malodour.

It is known that fresh sweat is odourless and that odour is only formed upon contact of sweat with skin bacteria (for example bacteria of the genera of *Staphylococcus* and *Corynebacteria*) and it is believed that odourless molecules present in sweat are degraded by bacteria colonising the axilla. It is generally accepted (Labows et. al., Cosmet. Sci Technol. Ser. (1999), 20:59–82) that highly unpleasant malodour is released from fresh sweat mainly by the *Corynebacteria* genus of bacteria. The principal constituents thought to be responsible for malodour include volatile steroids, volatile sulphur compounds and short-chain, branched fatty acids.

It has been suggested to treat malodour by eradicating the bacteria responsible for causing the odour. Indeed, commercially available cosmetic deodorants often contain antibacterial compounds that generally inhibit the growth of skin microflora. Antibacterial compounds currently used in deodorant products include, for example Triclosan (2,4,4'-trichloro-2'hydroxy-diphenyl-ether). However, a draw-back to the use of antibacterials is the potential for disturbing the equilibrium of the skin's natural microflora.

It has also been suggested to include compounds in a deodorant that would specifically target and suppress the biochemical reactions that transform odourless precursors present in sweat into volatile malodorous steroids or sulphur compounds. Specifically, there have been several publications concerned with the inhibition of enzymes that are thought to be responsible for the release of volatile steroids or volatile sulphur products. In this regard see U.S. Pat. Nos. 5,487,886; 5,213,791 and 5,595,728 which describe amino acid β-lyase inhibitors for use in deodorants. These agents are thought to block the release of sulphur volatiles from cysteine derivatives. U.S. Pat. Nos. 5,676,937 and 5,643,559 describe inhibitors of bacterial exoenzymes, namely sulphatases and glucuronidases. These compounds are supposed to reduce the release of volatile steroids from the corresponding sulphates or glucuronides. Patent application WO 00/01355 describes inhibition of steroid reductases. Finally, in German patent applications DE 19858811A1 and DE 19855956A1 the use of esterase inhibitors as deodorant active ingredients is described.

However, fatty acids, in particular short chain, branched fatty acids are known to play a role in axillary malodour, and are particularly foul smelling. Whereas WO 00/01356 attributes axillary malodour to the catabolism of long-chain fatty acids and teaches the use of certain perfumes to inhibit such catabolism, the art does not reflect an appreciation of the enzymatic process resulting in the release of malodorous fatty acids, in particular short chain, branched fatty acids and therefore does not teach how malodour from these sources may be prevented or suppressed.

The applicant has now discovered the mechanism of the release of fatty acids in sweat and has found an enzyme thought to be responsible for transforming odourless precursor compounds found in sweat, into malodorous fatty acids. The applicant has also found specific inhibitors of the enzyme and screening tools for identifying potential inhibitors, and also methods and compositions for preventing or suppressing malodour. These and other aspects of the present invention will become apparent to those skilled in the art from the following description.

The invention provides in a first aspect an enzyme that mediates in a biochemical process whereby essentially odourless precursor compounds found in sweat are cleaved to release malodorous compounds, particularly malodorous fatty acids, more particularly malodorous short chain, branched fatty acids.

The enzyme of the present invention was isolated from the bacteria of the genus *Corynebacteria* that can be found colonising the axilla, in particular certain *Corynebacteria* sp., more particularly *Corynebacteria striatum* Ax 20 which has been submitted on the 26, Apr. 2001 to the International Depository Authority DSMZ-Deutsche Sammlung Von Mikrooganismen Und Zellkulturen GmbH, D-38124 Braunschweig. The Accession Number provided by the International Depository Authority is DSM 14267.

The enzyme has not heretofore been available in isolated form. By "isolated" is meant that the enzyme is removed from its original environment, i.e. from the environment in which it is naturally occurring. The present invention therefore provides the enzyme in isolated form, more particularly in isolated, purified form. By "purified form" is meant at least 80%, more particularly greater than 90%, still more particularly 95%, most particularly 99% or greater with respect to other protein and/or nucleic acid contaminants. The enzyme may be characterised by the amino acid sequence set forth in SEQ ID NO: 1. However, also included in the scope of the invention are proteins or polypeptides, e.g. enzymes that comprise amino acid sequences that are substantially similar to the amino acid sequence as set forth in SEQ ID NO: 1. In its broadest sense, the term "substantially similar" when used in relation to an amino acid sequence, means a sequence corresponding to a reference amino acid sequence, wherein said corresponding sequence encodes for a polypeptide or protein, e.g. an enzyme having substantially the same structure and same function as the enzyme encoded for by the reference amino acid sequence. The percentage identity in sequences may be for example, at least 80%, particularly at least 90% and most particularly at least about 95% of the amino acid residues match over a defined length of the molecule and includes allelic variations. Sequence comparisons may be carried out using a Smith-Waterman sequence alignment algorithm which is known in the art.

Partial amino acid sequences of the enzyme set forth in SEQ ID NO: 2; NO: 3, and NO: 4 comprise additional aspects of the invention.

The amino acid sequence set forth in SEQ ID NO: 1 may be derived from the open reading frame contained in SEQ ID NO: 5. Accordingly, the invention provides in another of its aspects an isolated nucleic acid, for example set forth in SEQ ID NO: 5, encoding for an enzyme having an amino acid sequence set forth in SEQ ID NO: 1.

All sequence data may be obtained according to techniques commonly known in the art.

An enzyme of the present invention may have a molecular weight of 43 to 48 kDa. In particular, it may have an apparent molecular mass on SDS-PAGE of 48 kDa and an effective molecular mass of 43365 Da as determined by nano-ESI MS (electron spray ionisation mass spectrometry) analysis and also derived from the amino acid sequence.

An enzyme of the present invention mediates in a biochemical process whereby essentially odourless precursor compounds are cleaved to release malodorous compounds characteristically found in sweat. The precursor compounds are substrates that may generally be described as derivatives of L-glutamine, in particular L-glutamine derivatives wherein the $N_\alpha$ atom of the L-glutamine residue is acylated with a residue of a malodorous compound, in particular a fatty acid residue, more particularly a short chain, branched fatty acid residue. One example of such a precursor compound that was isolated from human sweat has the structure:

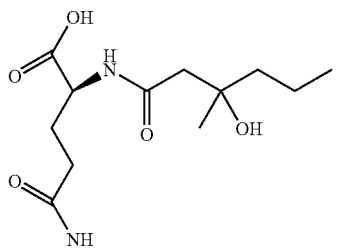

Cleavage of this substrate at the $N_\alpha$ position releases the 3-hydroxy-3-methyl-hexanoic acid, itself having a pungent odour, which dehydrates to give 3-methyl-3-hexenoic acid which is another key malodour volatile in human sweat. Proteins or polypeptides, e.g. enzymes that act to cleave substrates of the type referred to hereinabove to release malodorous acids are within the ambit of the present invention.

An enzyme according to the present invention may be particularly active in relation to certain substrates. For example, it can recognise $N_\alpha$-acylated-L-glutamine substrates. However, it is not able to cleave similar acylated derivatives of related amino acids such as L-glutamate, L-asparate or L-asparagine; nor does it recognise substrates wherein the $N_\delta$ or the COOH group of the L-glutamine moiety is substituted. Furthermore, it is stereospecific, for example it recognises derivatives of L-glutamine and not the analogues derived from D-glutamine. Having regard to the substrate specificity, an enzyme of the present invention may be described as an aminoacylase, more particularly, an $N_\alpha$-acyl-glutamine-aminoacylase. The acyl group at the $N_\alpha$ atom can vary widely, and the enzyme may cleave substrates for a wide variety of different smelling and non-smelling acids and other compounds. It may also, in addition to amide bonds, cleave carbamate bonds at the $N_\alpha$ position thereby mediating in the release of an alcohol, $CO_2$ and L-glutamine. It may also cleave acylated derivatives of L-glutamine where the $N_\alpha$ atom has been replaced by an oxygen atom, i.e. oxo-glutamine-derivatives.

Further, the enzyme requires as a cofactor a zinc ion. In this respect and in its ability to cleave amide-bonds, it may be considered to be related to the group of enzymes known as zinc-metallopeptidases. More specifically, since it may cleave an amide-bond situated next to a terminal carboxyl group, it may also be considered to be related to the group of enzymes known as the zinc-carboxypeptidases.

Whereas an enzyme of the present invention is highly selective for the glutamine residue of a substrate, as mentioned above, applicant has surprisingly found that a wide variety of glutamine derivatives are able to fit into the enzyme. For example applicant found that disparate substrates such as $N\alpha$-(3-hydroxy-3-methyl-hexanoyl)-L-glutamine, $N\alpha$(3-methyl-2-hexenoyl)-L-glutamine, $N\alpha$-lauroyl-L-glutamine, $N\alpha$-(11-undecenoyl)-L-glutamine, $N\alpha$-tetradecanoyl-L-glutamine, $N\alpha$-decanoyl-L-glutamine, $N\alpha$-phenylacetyl-L-glutamine, $N\alpha$-Carbobenzyloxy-L-glutamine (=Z-glutamine), $N\alpha$-3,7-Dimethyl-6-octenyloxycarbonyl-L-glutamine, $N\alpha$-(3-hexenyl)oxycarbonyl-L-glutamine, $N\alpha$-Butyloxycarbonyl-L-glutamine, $N\alpha$-(4-tert-Butylcyclohexyloxycarbonyl)-L-glutamine, $N\alpha$-2-Phenylethyloxycarbonyl-L-glutamine, $N\alpha$-(3-Methyl-5-phenylpentanoxycarbonyl)-L-glutamine, $N\alpha$-(2-Adamantan-1-yl-ethoxycarbonyl)-L-glutamine, $N\alpha$-(2-Adamantan-1-yl-methoxycarbonyl)-L-glutamine, $N\alpha$-[2-(2,2,3-trimethyl-cyclopent-3-enyl)-ethoxycarbonyl)-L-glutamine, and $N\alpha$-(4-methoxy-phenylsulfanylcarbonyl)-L-glutamine are all able to be cleaved by enzyme. These findings, together with knowledge as to the nature of metallopeptidases, suggest that an enzyme of the present invention has a high specificity for glutamine at its so-called "$S_1'$-site", but will accept a wide variety of substituents at the $N\alpha$-atom of the substrate provided those substituents are sufficiently bulky and hydrophobic to be received into the so-called "$S_1$ site" of the enzyme. The terms "$S_1$ site" and "$S_1'$ site" as used herein relate to the sites on metallopeptidase enzymes as will be apparent to a person skilled in the art.

An enzyme described hereinabove represents a particularly preferred embodiment of the present invention. However, other bacterial strains, for example other strains of *Corynebacteria*, or bacteria of the genus *Staphylococci* found in the microflora of the axilla also produce related enzymes that themselves mediate in biochemical reactions wherein L-glutamine derivatives are cleaved at $N_\alpha$. However, these related enzymes specifically cleave precursor compounds to release straight chain fatty acids, which acids play only a minor role in typical axilla malodour. These related enzymes, and inhibitors thereof, also form embodiments of the present invention.

A further aspect of the invention comprises a method of isolating an enzyme described above. Enzyme of the present invention occurs intracellularly and can be released from the cells by mechanical disruption of the cell envelope. Thus, an enzyme may be isolated from cellular extracts obtained from wild-type bacterial strains, especially from strains of *Corynebacteria* isolated from the human axilla, in particular *Corynebacterium striatum* Ax 20.

Alternatively, an enzyme may be manufactured by recombinant means and the invention provides in another of its aspects such methods, recombinant vectors and their use as reagents in said manufacture, and procaryotic or eurocaryotic host cells transformed with said vectors.

Thus, an enzyme may be produced by growing host cells transformed by an expression vector comprising foreign nucleic acid that encodes for the enzyme under conditions such that it is expressed, and thereafter recovering it according to known techniques. In a particular embodiment of the invention a nucleic acid fragment that encodes for the SEQ ID NO: 5 or a substantially similar nucleic acid sequence coding for an enzyme with an amino acid sequence which is substantially the same as sequence SEQ ID NO 1, is introduced into an expression vector by operatively linking the nucleic acid to the necessary expression control regions required for gene expression. The vector is then introduced into an appropriate host cell, e.g. a bacterial host cell, more particularly *E.Coli*. Numerous expression vectors are known and commercially available, and the selection of an appropriate expression vector and suitable host cells which they can transform is a matter of choice for the skilled person. Examples of expression vectors and host strains are described in T. Maniatis et al. (Molecular Cloning, cold spring Harbor Laboratory, 1982), other examples of vector-host strain combinations are the vector pPROTet.E133 in strain DH5$_\alpha$PRO which may be obtained from Clontech (Palo Alto, Calif., USA) or the vector pBADgIIIA in strain TOP 10, which may be obtained from Invitrogen (Groningen, The Netherlands).

Recombinant production of an enzyme according to the invention is not limited to the production in bacterial hosts. Any other means known to those skilled in the art of producing an enzyme based on a defined genetic sequence may be used. Such methods include, for example the expression in genetically modified yeasts, in insect cells transformed with a modified baculovirus and in eucaryotic cell lines or the in vitro transcription and translation.

The enzyme produced according to methods described above may be purified according to known techniques. Thus, host-cells containing the enzyme may be extracted to release the enzyme, e.g. by mechanical disruption of the cells or by osmotic shock. Thereafter, crude enzyme may be separated from host cell debris and host cell protein and nucleic acid contaminants using well known techniques such as precipitation and chromatography. Any of the chromatography techniques known in the art for purifying proteins may be employed. For example, ion-exchange, hydrophobic interaction, reverse phase, and size exclusion chromatography steps may be employed in any suitable sequence. Optionally, after each chromatography step the eluted enzyme may be further purified by filtration and concentrated using, e.g. ultrafiltration techniques.

In another aspect of the invention there is provided a method of screening compounds as inhibitors of an enzyme as hereinabove described. In particular, in order to identify inhibitory compounds, the enzyme or cells or cell extracts containing the enzyme, obtained from any of the above described sources, may be incubated along with an appropriate substrate that is cleavable by the enzyme, and with potential inhibitory compounds. An appropriate substrate may be selected from any of the class of precursor compounds referred to hereinabove, in particular an $N_\alpha$-acylated L-glutamine or carbamate of glutamine. Particular useful substrates are $N_\alpha$-3-methyl-3-hydroxy-hexanoyl-glutamine, $N_\alpha$-lauroyl-L-glutamine (commercially available from Fluka, Buchs, Switzerland) and $N_\alpha$-carbobenzyloxy-L-glutamine (Z-glutamine; commercially available from Aldrich, Buchs, Switzerland). After a certain time of incubation, which may be determined according to routine experimentation, analysis may be performed by measuring the released acid or alcohol, or by measuring the amount of free L-glutamine. A particularly useful approach for high-throughput screening of potential inhibitors may be to measure the release of free L-glutamine by derivatising the free $N_\alpha$ group with an amine-group derivatising agent, which upon reaction with the amine group forms a chromophore or a fluorescent molecule. Particularly useful in this regard may be the use of fluorescamine (commercially available from Fluka, Buchs, Switzerland) to form a fluorescent molecule upon reaction with L-glutamine. Finally, the cleavage of the L-glutamine-substrate may be compared to control reactions and the potential of the test compounds to inhibit the reaction may thereby be quantified.

Having regard to the nature of the enzyme and the screening method set forth above the skilled person will be able to derive compounds that are inhibitors of the enzyme in its mediation in the biochemical reaction resulting in the release of malodorous compounds, and these inhibitors form yet another aspect of the invention.

Potential inhibitors may be selected, by way of non-limiting example, from dithiols, which molecules are capable of strongly co-ordinating to an active-site zinc atom located on the enzyme. One example of such a compound is dithiothreitol (2,3-dihydroxy-butane-1,4-dithiol). Other zinc chelators may be useful inhibitors; such chelating agents may include o-phenanthroline, EDTA, Na-pyrithione, amino-tri(methylene-phosphonic acid), ethylene-diimino-dibutyric acid (EDBA), Ethylenediamine-2-2'-diacetic acid, pyridine-2,6 dicarboxylic acid, Diethylenetriamine pentaacetate, Ethylenediamine disuccinic acid, and N,N,N',N'-tetrakis-(2-pyridylmethyl)-ethylenediamine. A further group of inhibitors may be selected from $N\alpha$-actl-L-glutamines or carbamates of L-glutamine which introduce some steric hindrance into the moiety substituted at the $N_\alpha$ atom. These inhibitors may compete with the natural precursor compounds found in sweat for the active zinc site on the enzyme, but display a reduced tendency, or no tendency, relative to the natural precursor compound, to cleave at the $N_\alpha$ atom.

Compounds of formula (I)

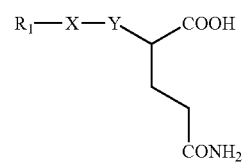

have been found to be particularly interesting inhibitors of the enzyme and these compounds form a preferred embodiment of the present invention.

In formula (I), Y represents a direct bond to X, or a divalent chain that may contain carbon, oxygen or nitrogen atoms, and may comprise functionality such as amide functionality —CONH— provided that the chain is not cleavable by the enzyme under condition of use. Preferably this divalent chain contains no more than 3, and preferably no more than 2 atoms in the chain.

X represents a zinc-chelating group, e.g. a group bearing carboxylic acid functionality, or more particularly a methylene thiol group (II), or a phosphinyl group (III)

As regards the group $R_1$, given the broad range of substituents that can fit into the $S_1$ site of the enzyme, the nature of this group may vary widely provided it is sufficiently hydrophobic and/or bulky to fit into this site. Preferably, it represents a linear, branched or cyclic carbon chain having about 1 to 14 carbon atoms, more particularly about 4 to 14 carbon atoms. The aforementioned chain may contain one or more heteroatoms such as O, N or S, and it may also contain unsaturation. The chain may support one or more substituents, for example amide, ester, keto, ether, amine or hydroxyl halogen, or aryl or heteroaryl substituents which aryl or heteroaryl groups may support substituents selected from amide, ester, keto, ether, amine, halogen, alkyl or hydroxyl. The term "aryl" or "heteroaryl" as used herein is preferably a mono-cyclic or polycyclic group containing from 6 to 14 carbon atoms, and as appropriate one or more heteroatoms such as O, N or S. By way of example, any of the substituents attached to the acyl carbonyl group of the substrates mentioned above would be suitable as a group $R_1$.

More preferred groups $R_1$ may be selected from a $C_{1-14}$ alkyl, more preferably a $C_{4-14}$ alkyl, e.g. n-butyl or sec-butyl, or an alkyl group here-mentioned substituted with a phenyl group, or a phenyl group substituted with any of the substituents referred to above, e.g. a benzylic group or a phenylethyl group.

More preferred compounds of formula (I) are those compounds wherein
Y is selected from a direct bond to X, $C_{1-3}$ alkylene, e.g. methylene, —CONH—, or —NH—, and
X is selected from methylene thiol (II) or phosphinyl (III).

Most preferred compounds of the present invention are those compounds of formula (I) wherein
Y represents an amide group —CONH— when X is methylene thiol (II) or Y represents a methylene group when X is phosphinyl (III).

Compounds of formula (I) contain chiral atoms and as such they can exist as diastereomeric mixtures or they may exist as pure stereo-isomers. Most preferred compounds have an S-configuration on the Glutamine moiety, and in the case of the methylene-thiol containing compounds also an S-configuration at the chiral centre in this group is preferred.

Examples of most preferred compounds are

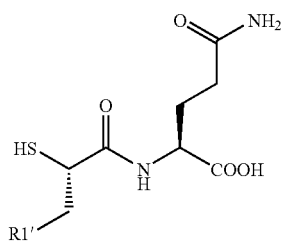

wherein R1' is phenyl (5a); iso-$C_3H_7$ (5b); or n-$C_3H_7$ (5c); or,

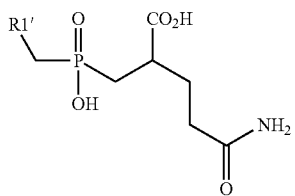

wherein R1' is phenyl (8a); iso-$C_3H_7$ (8b); or n-$C_3H_7$ (8c).

The compounds of the present invention may be synthesised by coupling together the amino acid residue, e.g. the glutamine residue with the residue $R_1$—X—Y— according to methods known in the art using readily available starting materials or reagents.

The N-(sulfamylacyl)amino acids exemplified as (5a–c) above may be prepared in a manner set forth in Scheme I of FIG. 1. The t-butyl ester of glutamine may be coupled in a classical procedure of liquid-phase peptide synthesis using EDCI+HOBT with various acetylsulfamyl alkanoic acids (2) leading to (3). After deprotection of the t-butyl ester group and hydrolysis of the acetylsulfamyl group, one may obtain the compounds (5). The various acetylsulfamyl alkanoic acids (2) may be obtained form the corresponding alpha amino acids. Brominative deamination leads to the removal of the alpha-amino functionality replacing it with a bromine atom with retention of configuration. Subsequent removal of the bromine atom with the potassium salt of thioacetic acid will provide a compound (2) with inversion of configuration.

The skilled person will appreciate that other N-acylated glutamine compounds of the present invention may be synthesised in an analogous manner using appropriate reagents to provide the desired $R_1$—X—Y-residue.

Figure 2:
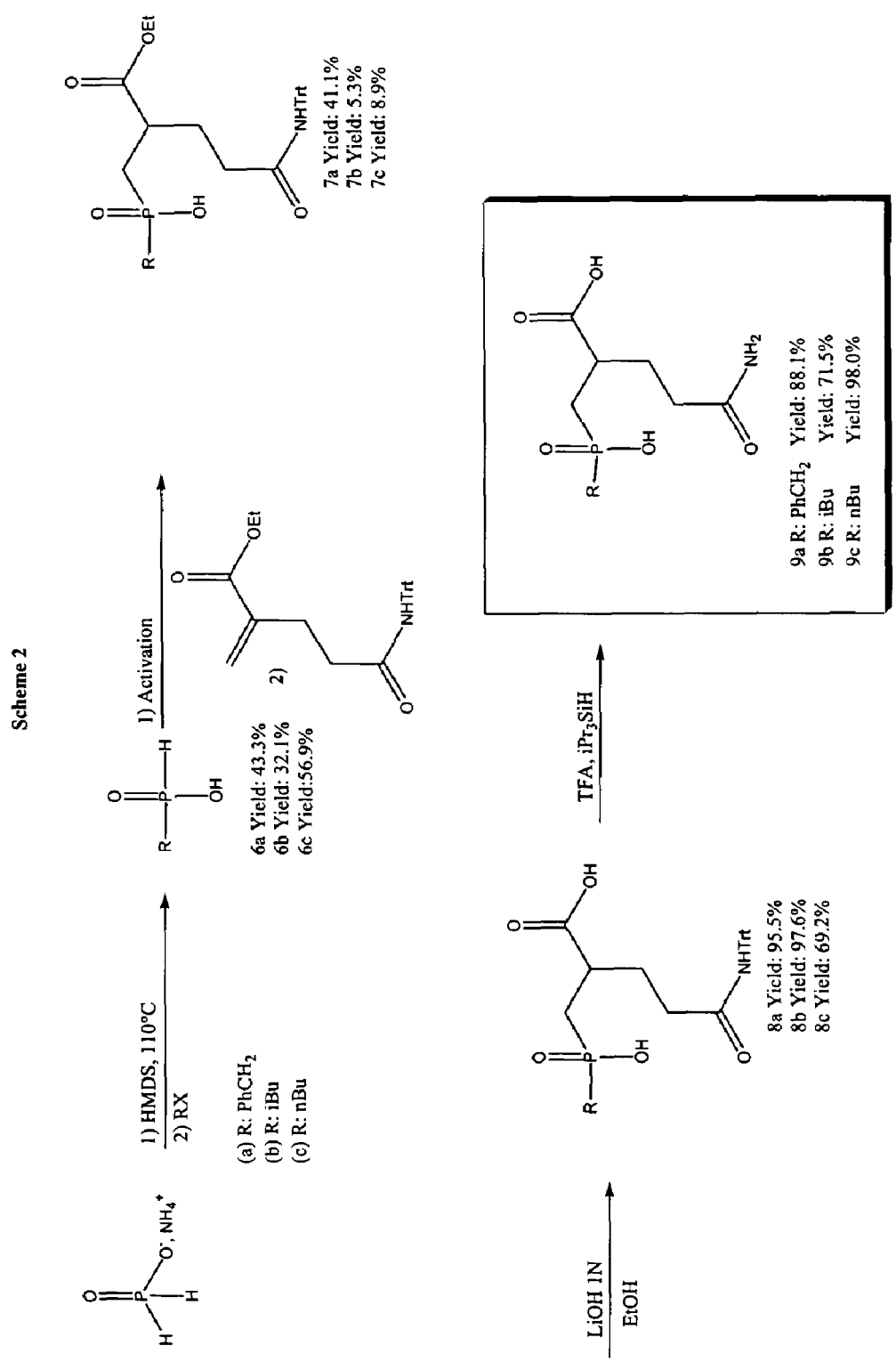

The phosphinic-type compounds may be prepared by condensation of a desired alkyl halide and phosphinic acid ammonium salt to give a compound (6), followed by a 1,4 addition of (6) to the ethyl-2-(N-trityl)carboxamidoethyl acrylate as set forth in Scheme 2 of FIG. 2. Deprotection of the ester group and the amide can be achieved in manner known per se to form the desired compound. The acrylate compound may be formed according to a method set forth in Scheme 3 of FIG. 3. The skilled person will appreciate that other compounds of the present invention can be produce by 1,4 addition of a residue bearing $R_1$—X—Y— with the aforementioned acrylate.

Further details regarding the synthesis of compounds of the present invention are disclosed in the Examples hereinbelow.

Applicant has disclosed a wide range of compounds with inhibitory properties. However, having regard to the wide substrate specificity of the enzyme of the present invention responsible for the release of the malodorous compounds found in sweat, and the reliable methodology for identifying inhibitors of the enzyme, the applicant is able to provide a novel method in the suppression of body odours which methods form an additional aspect of the invention.

Accordingly, the invention provides in another of its aspects, a method of suppressing axillary malodour comprising the step of providing a composition for application to a person in need of treatment, said composition containing an inhibitor compound and dermatologically acceptable vehicle therefor, said compound being selected from a screening of compounds for activity in the inhibition of the enzyme.

Compounds, which inhibit an enzyme of the present invention reduce the activity of the enzyme and may lead to a significant reduction of the release of malodour acids from odourless fresh sweat. Compounds of the present invention display inhibition of the enzyme at concentrations ranging from $10^{-3}$ to $10^{-8}$ Molar. The activity of the compounds as inhibitors may be measured in terms of either their $IC_{50}$ values or their Ki values, both of which measures are well known to the person skilled in the art. As is well known, the $IC_{50}$ value provides the concentration of an inhibitor needed to reduce enzyme velocity by half at a given substrate concentration. This value is dependent on the affinity of the substrate for the enzyme which is reflected in the value $K_m$ of the substrate. In this way, the Ki value may be determined for a given substrate and a given substrate concentration by measuring $IC_{50}$ and then calculating according to the following formula $$K_i = \frac{IC_{50}}{1 + \frac{[Substrate]}{K_m}}$$

Ki values for certain preferred inhibitors are set forth in Example 8 below.

Compounds of the present invention may be added to any cosmetic and personal care products such as sticks, roll-ons, pump-sprays, aerosols, deodorant soaps, powders, solutions, gels, creams, sticks, balms and lotions to enhance the deodorising effect of these products.

Accordingly, the present invention relates to the use of inhibitor compounds in compositions for the elimination or suppression of malodour. The invention also relates to compositions comprising an odour suppressing quantity of an inhibitor of the enzyme and dermatologically acceptable vehicles which are generally well known in the art of cosmetic and personal care products and require no further elaboration here. Preferably, a compound of the present invention may be employed in said products in amounts of about 0.01 to 0.5% by weight.

In an alternative method of malodour prevention or suppression, instead of, or in addition to, employing inhibitors that act to prevent or suppress the activity of the enzyme, one may employ agents that reduce the expression of the enzyme in bacteria containing a gene coding for said enzyme. Such agents may be screened either using wild-type strains or genetically engineered strains of the bacteria expressing the enzyme. If wild-type strains are used, the level of enzyme expression may be directly measured under various environmental conditions and upon addition of potential inhibitory compounds. Alternatively, genetically engineered Corynebacteria that are transformed with a vector containing a reporter gene may be used. These vectors may contain the reporter gene under the control of the regulatory sequences for the enzyme expression, which regulatory sequence is contained in the SEQ ID NO: 6 and which forms another aspect of the invention. For this purpose, the regulatory sequence, or any part thereof, may be cloned upstream of the reporter gene into a broad host-range vector able to transform Corynebacteria. The reporter gene may thereby be put under the regulatory control of the genetic sequence which controls the expression of the enzyme. The vector obtained in this way may then transformed into a strain of Corynebacterium. Particularly useful vectors for this purpose are described by M. P. Schmitt (Infection and immunity, 1997, 65(11): 4634–4641) and by N. Bardonnet and C. Blanco (FEMS Microbiol Lett., 1991, 68(1):97–102). Particularly useful marker genes are lacZ (coding for β-galacturonidase, gfp (coding for the green fluorescent protein), luxABCD (coding for bacterial luciferase) and gusA (coding for glucuronidase). The genetically engineered strain may then be grown in the presence of a compound to be tested and the expression of the marker gene may be measured by conventional methods. Compounds that lead to a reduction in expression (i.e. reduce the level of mRNA) may reduce malodour formation by reducing the level of enzyme in the axilla.

There now follows a series of examples that serve to illustrate the invention.

EXAMPLE 1

Isolation of New Malodour Acid and Precursors thereof from Human Sweat

Fresh axilla secretions were sampled from human panellists by washing the axilla with 10% ethanol. The samples were extracted with MTBE to remove interfering lipids. The hydrophilic phases obtained from the washings from several individuals were then pooled. This material was practically odourless, but upon hydrolysis of sub-samples with 1 M NaOH, it produced typical axilla malodour. To identify the malodour volatiles, hydrolysed sub-samples were extracted and concentrated by solid phase extraction and then analysed by GC-sniff. Peaks that were rated as having a strong odour and closely related to axilla malodour were analysed by GC-MS. The samples contained one particular peak of an acid very typical of axilla malodour. Based on the MS data the most probable structure of this peak was 3-hydroxy-3-methyl-hexanoic acid. This assumption was verified by synthesising this latter compound and comparing its spectra and retention times to the GC-MS data of the major malodour peak in the GC-sniff analysis. This new malodour compound is structurally related to the known sweat malodour acid 3-methyl-2-hexenoic acid, and it is transformed into this latter compound by dehydration upon prolonged incubation.

To identify the precursor for this acid, the pooled non-hydrolysed sample was separated on a Superdex gel filtration column (Pharmacia, Uppsala, Sweden) using $NH_4CO_3$/NaCl as the elution buffer. Individual fractions of this separation step were tested for the content of a malodour precursor by hydrolysis with 1 M NaOH. One fraction developed strong malodour upon hydrolysis and this malodour could be attributed to the release of 3-hydroxy-3-methyl-hexanoic acid by GC-MS analysis. This fraction was subjected to LC-MS analysis. It contained one major mass peak of 274 Da and an additional peak at 256 Da. The mass spectrum of the former peak suggested a compound where the 3-hydroxy-3-methyl-hexanoic acid is linked to one molecule of L-glutamine (i.e. $N_\alpha$-3-hydroxy-3-methyl-hexanoyl-L-glutamine), while the second peak could, based on its mass, correspond to the dehydrated analogue $N_\alpha$-3-methyl-2-hexenoyl-L-glutamine. $N_\alpha$-3-hydroxy-3-methyl-hexanoyl-L-glutamine was then synthesised and its MS spectrum and retention time in the LC-MS-analysis compared to and found identical with the compound isolated from natural sweat.

EXAMPLE 2

Isolation of Axilla Bacteria having the Ability to Cleave the Malodour Precursor Compound The axillary flora of 8 panellists was isolated with the detergent-scrub method: A 6 $cm^2$ area of the axilla was scrubbed with a phosphate buffer at pH 7 containing 1% Tween 80. The samples were spread-plated on tryptic soy agar amended with 5 g/L of Tween 80 and 1 g/L of lecithin. Single isolates obtained after 48 h incubation were subcultured and characterised. A total of 24 individual strains were identified based on colony and cell morphology, gram-reaction, lipophilic growth, lipase reaction and API identification kits (bioMerieux, France; coryneforms with the API coryne kit and cocci with the ID Staph 32 kit). The strains were grown overnight in a liquid medium (Mueller-Hinton amended with 0.01% Tween 80), harvested by centrifugation and resuspended to a final $OD_{600}$ of 1 in a semi-synthetic medium (Per litre: 3 g $KH_2PO_4$, 1.9 g $K_2HPO_4$, 0.2 g yeast extract, 0.2 g $MgSO_4$, 1.4 g NaCl, 1 g $NH_4Cl$, 10 mg $MnCl_2$, 1 mg $Fe_3Cl_2$, 1 mg $CaCl_2$). Aliquots of this stationary culture were then amended with a final concentration of 500 ppm of $N_\alpha$-3-hydroxy-3-methyl-hexanoyl-L-glutamine (5% stock solution dissolved in methanol). After 24 h incubation (with shaking at 300 rpm; 36° C.) the samples were extracted and the amount of released 3-hydroxy-3-methyl-hexanoic acid was determined by capillary GC. Table 1 gives the results for a subset of the strains tested. From these results it appears that among the *Corynebacteria* isolated from the axilla some, but not all, are able to release 3-hydroxy-3-methyl-hexanoic acid form the synthetic precursor. The *Corynebacteria* which are able to conduct this biochemical reaction may be found in the group of the lipophilic and in the group of the non-lipophilic *Corynebacteria*. Therefore, a specific enzyme only present in some bacterial strains seems to be responsible for this cleavage. Since it releases axilla malodour the putative enzyme was named AMRE, which stands for 'axillary malodour releasing enzyme'. Apparently the tested *Staphylococci* are not able to catalyse this reaction, which is in agreement with the observation, that only subjects with an axilla flora dominated by *Corynebacteria* produce the most typical axilla malodour (Labows et. al., Cosmet. Sci Technol. Ser. 1999, 20:59–82). However, when Nα-lauroyl-L-glutamine was used as substrate in the same experiment, it was found that also other *Corynebacteria* and some *Staphylococci* can release lauric acid from this substrate. It therefore appears, that most axilla bacteria have a related enzyme, but that many can only release straight fatty acids which make a minor contribution to typical axilla malodour.

TABLE 1

Cleavage of the natural malodour precursor by axilla bacteria.

| Isolate | Species assignment | Lipophilic (*) | 3-hydroxy-3-methyl-hexanoic acid released (ppm) |
|---|---|---|---|
| Ax1 | *Staphylococcus capitis* | − | 0 |
| Ax6 | *Staphylococcus epidermidis* | − | 0 |
| Ax9 | *Micrococcus luteus* | − | 0 |
| Ax3 | *Corynebacterium bovis* | + | 0 |
| Ax7 | *Corynebacterium* group G | + | 0 |
| Ax15 | *Corynebacterium jeikeium* | + | 37.4 |
| Ax19 | *Corynebacterium jeikeium* | + | 105.1 |
| Ax20 | *Corynebacterium striatum* | − | 262.7 |

(*) Corynebacteria isolated from the human axilla may be separated into two classes based on their requirement for a source of fatty acids in the growth medium.

EXAMPLE 3

Purification and Analysis of the Enzyme from Strains that Cleave Malodour Precursor Compounds

*Corynebacterium striatum* Ax20 was selected to isolate and purify the enzyme responsible for the cleavage of the precursor Nα-3-hydroxy-3-methyl-hexanoyl-L-glutamine. The strain was grown during 48 h in Mueller-Hinton broth amended with 0.01% Tween 80. A total volume of 2 L of culture was harvested by centrifugation. The pellet was washed in Buffer A (50 mM NaCl; 50 mM $NaH_2PO_4$/$K_2HPO_4$ buffer at pH 7) and this buffer was used throughout the whole purification procedure. The cells were disrupted mechanically by vortexing them with glass beads (425–600 μm, Sigma, St-Louis, USA) during 30 min at maximal speed. The crude cell lysate was then fractionated by precipitation with an increasing concentration of $(NH_4)_2SO_4$. The precipitate obtained between 50% and 80% saturation of $(NH_4)_2SO_4$ contained the active enzyme. This enriched sample was dissolved in Buffer A and then sequentially passed over four chromatography columns: DEAE Sepharose CL-6B anion exchange resin (Pharmacia, Uppsala, Sweden; elution with a linear gradient from 0 to 800 mM KCl); Phenyl-Sepharose hydrophobic interaction resin (Pharmacia; elution with a linear gradient from 1000 mM to 0 mM of $(NH_4)_2SO_4$; Mono Q strong anion exchange column on the FPLC system (Pharmacia; elution with a gradient from 0 to 800 mM KCl) and finally Mono P weak anion exchange column on the FPLC (elution with a gradient from 0–800 mM KCl in a 50 mM Bis-Tris buffer instead of Buffer A). After each column separation the active fractions (determined by fluorescent activity assay with Nα-lauroyl-L-glutamine as substrate, see example 8) were pooled and then desalted and concentrated by ultrafiltration (Amicon membrane YM10, Millipore, Bedford, US). The resulting active fractions after the last column separation contained one major protein band with an apparent molecular weight of about 48 kDa as determined by SDS-PAGE. Its effective molecular mass was determined by nano-ESI MS analysis and found to be 43365±5 Da. This enzyme retained all its activity if incubated with PMSF (Phenylmethylsulfonylfluoride, Roche Biochemicals, Mannheim, Germany) and Pefabloc SC (4-(2-aminoethyl)-benzenesulfonylfluoride, Roche Biochemicals), which are typical inhibitors for serin- and cystein proteases. On the other hand it was completely inhibited by 1 mM of EDTA and o-phenantrolin. This inhibition could be reversed by the addition of 1 mM $ZnCl_2$. This indicates that the enzyme belongs to the class of zinc-dependent metallo-peptidases, requiring a Zn atom as cofactor. Finally, the enzyme was subjected to LC-ESI-MS/MS analysis after tryptic digestion and to analysis of its N-terminal amino acid sequence. This led to identification of its N-terminal amino acid sequence (SEQ ID NO: 2) and to the sequence of two internal peptides (SEQ ID NO: 3; SEQ ID NO: 4).

EXAMPLE 4

Substrate Specificity of the Enzyme

To understand in detail the structural requirements of substrates, the enzyme extracted from *Corynebacterium striatum* Ax20 was incubated with a wide variety of said compounds related to the originally isolated $N_\alpha$-3-methyl-3-hydroxy-hexanoyl-L-glutamine present in sweat. Each compound was used at a concentration of 500 ppm in Buffer A, and analysis of released acid or alcohol was done by capillary GC after 24 h of incubation. First, different modifications at the N-terminus were tested. It was found, that the enzyme can cleave such simple substrates as $N_\alpha$-lauroyl-L-glutamine and $N_\alpha$-carbobenzyloxy-L-glutamine (=Z-glutamine). From the latter it releases benzyl-alcohol. Other N-lauroyl-amino acids and Z-amino acids (all obtained from Fluka and Aldrich, Buchs, Switzerland) were thus tested, but it was found that among the 20 amino acids occurring in proteins, the enzyme only cleaves L-glutamine derivatives, and, to much lesser extent, L-alanine derivatives. The results of some of the substrates tested are summarised in Table 2. Furthermore the enzyme can cleave other carbamates of L-glutamine, also derivatives where the alcohol is a fragrance alcohol (for example citronellol, see Table 2 compound 5), and it can therefore be used to release pleasant smelling molecules from precursors. Indeed, it has broad specificity for substituents at $N_\alpha$ as reflected in compounds 1–5 (below) and as discussed above. Finally, it is stereospecific and cannot cleave derivatives of D-glutamine (Table 2, compound 19), it requires a free COOH group of the L-glutamine and does not cleave derivatives in which this group is linked to methanol or glycin (Table 2, compounds 20 and 21). It also cannot cleave a derivative in which the $N_\delta$ of glutamine is further derivatised (Table 2, compound 22).

TABLE 2

Substrate specificity of the enzyme

| Substrate | Cleavage by enzyme[1] |
|---|---|
| 1  Nα-(3-hydroxy-3-methyl-hexanoyl)-L-glutamine | ++ |
| 2  Nα-lauroyl-L-glutamine | +++ |
| 3  Nα-decanoyl-L-glutamine | +++ |
| 4  Carbobenzyloxy-L-glutamine | ++ |
| 5  $N_\alpha$-3,7-Dimethyl-6-octenyloxycarbonyl-L-glutamine | +++ |
| 6  N-Lauroyl-L-aspartate | – |
| 7  Nα-Lauroyl-L-lysine | – |
| 8  Nα-Lauroyl-L-arginine | – |
| 9  N-lauroyl-L-alanine | + |
| 10  Carbobenzyloxy-L-alanine | + |
| 11  Carbobenzyloxy-L-glutamate | – |
| 12  Carbobenzyloxy-L-asparagine | – |
| 13  Carbobenzyloxy-L-aspartate | – |
| 14  Carbobenzyloxy-L-serine | – |
| 15  Carbobenzyloxy-L-tyrosine | – |
| 16  Carbobenzyloxy-L-glycine | – |
| 17  Carbobenzyloxy-L-histidine | – |
| 18  Carbobenzyloxy-L-leucine | – |
| 19  Carbobenzyloxy-D-glutamine | – |
| 20  Carbobenzyloxy-L-glutamine-O-Me | – |
| 21  Carbobenzyloxy-L-glutamine- Gly-OH | – |
| 22  4-benzylcarbamoyl-2-(S)-benzyloxyamino-butyric acid | – |

[1]– indicates no cleavage, + indicates cleavage < 10%, ++ cleavage 10–50% and +++ cleavage over 50%.

EXAMPLE 5

Isolation of the Gene Coding for the Enzyme

Based on the partial amino acid sequence analysis (see example 3), degenerated primers were designed and used to amplify a 350 bp and a 650 bp fragment of the corresponding gene between the N-terminus (SEQ ID NO 2) and the two internal peptide sequences (SEQ ID NO 3 and 4). Chromosomal DNA of Ax20 served as template. The primer with the sequence SEQ ID NO 7 successfully annealed at the sequence coding for the N-terminus and the primers with the sequence SEQ ID NO 8 and SEQ ID NO 9 annealed within the sequences coding for the internal peptides. Standard PCR conditions were used, and the annealing temperatures were optimised on a gradient cycler (T-Gradient, Biometra, Göttingen, Germany). The amplified DNA was cloned into the vector pGEM-T Easy (Promega, Madison, USA) and the nucleotide sequence determined on the ABI-Prism model 310 (PE Biosystems, Rotkreuz, Switzerland) using standard methods. Based on the obtained sequence, specific nested oligonucleotides were designed to clone the upstream (SEQ ID NO 10 and 11) and downstream region (SEQ ID NO 12 and SEQ ID NO 13). Chromosomal DNA of Ax20 was digested with SmaI and PvuII and ligated to the GenomeWalker Adaptor (Clontech Laboratories, Palo Alto, USA). The upstream and downstream regions were then amplified as described in the instructions to the Universal GenomeWalker™ kit (Clontech Laboratories, Palo Alto, USA), cloned into the vector pGEM T-easy and the nucleotide sequence determined. With the two enzyme digests two upstream (450 bp and 1200 bp) and two downstream fragments (1200 bp and 3000 bp) were obtained. The full coding sequence of the enzyme (SEQ ID NO 5) as well as upstream (SEQ ID NO 6) and downstream regions were contained in the cloned region. The deduced amino acid sequence of the open reading frame corresponding to the enzyme (SEQ ID NO 1) was compared to public protein sequence databases (Swissprot and GeneBank, bacterial sequences) and it was found to align very well to known aminoacylases, some carboxypeptidases and various putative peptidases identified in genome sequencing projects. A number of these enzymes are summarised into the peptidase family m40, also known as the ama/hipo/hyuc family of hydrolases.

EXAMPLE 6

Heterologous Expression of the Gene Coding for the Enzyme

The full-length sequence of the open reading frame coding for the enzyme was amplified with PCR from chromosomal DNA of Ax20 using specific primers (SEQ ID NO 14 and SEQ ID NO 15). The amplified DNA fragment was then digested with the restriction enzymes NcoI and Hind III It was then ligated into the vector pBADIIIA (Invitrogen, Groningen, The Netherlands) pre-digested with the same enzymes. The resulting plasmid pBADgIIIAMRE was transformed into the host strain *E. coli* TOP10 (Invitrogen). This strain was grown in LB broth until it reached an optical density of about 0.5 at 600 nm. The culture was induced with arabinose (0.2% final concentration) incubated for 4 h, harvested by centrifugation and disrupted by ultrasonication. Enzyme assays with Nα-lauryl-Glutamine as substrate were performed in Buffer A with an incubation time of 1 h and a substrate concentration of 500 ppm. Table 3 gives the activity of extracts obtained from wild-type cells and from extracts of the induced and non-induced modified strains expressing the enzyme.

TABLE 3

Heterologous expression of the enzyme in *E. coli*

| | release of lauric acid from Lauryl-Glutamine, 1 h incubation | | |
|---|---|---|---|
| | *E. coli* Top 10 | *E. coli* Top 10/ pBADgIIIAMRE not induced | *E. coli* Top 10 induced |
| 4 h after induction | below detection | 23 ppm | 329 ppm |

EXAMPLE 7

Low Throughput Screening for Inhibitors of the Enzyme

Extracts of Ax20 were prepared by mechanical disruption as described in Example 3. The extract (0.5 ml corresponding to 2 ml initial cell culture) was added to 3.5 ml of Buffer A and amended with 40 μl of substrate (Nα-lauroyl-L-glutamine, 5% stock solution in methanol). Parallel samples were additionally amended with potential inhibitory compounds to give a final concentration of 0.5 and 5 mM. The samples were incubated for 2 h and then extracted with MTBE and HCl and analysed for released lauric acid using capillary GC. By comparing the samples containing potential inhibitory compounds with control samples with enzyme and substrate only, the inhibition (%) was calculated. Table 4 gives the result for selected zinc chelating compounds. The same assay was also made either with purified enzyme from the wild-type strain (see example 3) or with extracts from *E.coli* Top 10/pBADgIII AMRE induced with arabinose (see example 6). Furthermore, the same assay was made using stationary phase living cells of Ax20 instead of an isolated enzyme preparation. In this case successful uptake of the inhibitors into the cells and inhibition are measured simultaneously.

TABLE 4

Inhibition by zinc chelators of the isolated enzyme and of the enzymatic activity in intact cells

|  | % inhibition of enzyme activity in living cells | % inhibition of the isolated enzyme | |
| --- | --- | --- | --- |
|  | 5 mM | 5 mM | 0.5 mM |
| o-phenantrolin | 90.3% | 100% | 100% |
| 2,2'-bipyridyl | n.d. | 65% | n.d. |
| Aminotri(methylene-phosphonic acid) | 55.7% | 76.6% | n.d. |
| Ethylen-diimino-dibutyric acid | 53.7% | 44.3% | n.d. |
| Ethylendiamine-2-2'-diacetic acid | 58.3% | 100% | n.d. |
| Pyridine-2,6dicarboxylic acid | 64.3% | 100% | n.d. |
| N,N,N',N'-tetrakis-(2-pyridylmethyl)-ethylendiamine | 85.2% | 87.9% | n.d. |
| Dithiothreitol | n.d. | 100% | 98% |

EXAMPLE 8

High Throughput Screening for Inhibitors of the Enzyme

Potential inhibitory compounds were dissolved in Buffer A and aliquots of the solutions of different inhibitors (10 µl) were distributed to individual wells of a white microtiter plate. Purified enzyme obtained from the strain *E.coli* Top 10/pBADgIII AMRE was diluted in Buffer A (200 pg/ml final concentration) and added to the inhibitory compounds. After 10 min preincubation, the substrate (Nα-lauroyl-L-glutamine) was added to the individual wells to a final concentration of 0.05 mM. After 15 min of incubation, the amino-group of the released L-glutamine was derivatised by adding to each well of the microtiter plate 50 µl of a fluorescamine stock solution (2.5 mM in acetonitrile; fluorescamine obtained from Fluka, Buchs, Switzerland). After 5 min the fluorescence in the wells of the microtiter plates was measured with an excitation wavelength of 360 nm and an emission wavelength of 460 nm. The fluorescence of control wells with enzyme, substrate and DMSO only was then compared to the fluorescence in wells containing potential inhibitors. By varying the inhibitor concentration, the IC50 value for each compound was determined, and the Ki values were calculated.

TABLE 5

Ki values for compounds of formula (I)

| Compound | Ki value (nM) |
| --- | --- |
| 5a | 54 ± 1 |
| 5b | 130 ± 10 |
| 5c | 410 ± 20 |
| 8a | 50 ± 3 |
| 8b | 58 ± 4 |
| 8c | 110 ± 10 |

SYNTHESIS EXAMPLE 1

The following description is made with reference to Scheme 1 in FIG. 1

Synthesis of the Thiol Inhibitors

Step 1—Synthesis of (2R)-2-Bromo-alkyl carboxylic acids (1)

In a synthesis based on Fisher, S. R. W.; *Justus Liebigs Ann. Chem.*, 1957, 357 , (0.165 mol) of the corresponding D-α-aminoacid are solubilised in 165 mL HBr 48% and 150 mL water. The reaction mixture is cooled to 0° C. and a solution of $NaNO_2$ (18.3 g , 1.6 eq) in 60 mL water is added dropwise. The mixture is stirred for 2.5 h at room temperature, then concentrated to remove the acid vapour, extracted with $Et_2O$ four times. The organic layers are washed with water, NaCl sat., dried over $Na_2SO_4$, and concentrated under reduced pressure yielded compound 1 as oil used without further purification.

1a, R: $PhCH_2$: Yield 100% Rf: 0.43 ($CH_2Cl_2$/MeOH/AA 9/1/0.2) $^1$H NMR ($CDCl_3$ 270 MHz): 7.3(m, 5H), 4.3(t, 1H), 3.1–3.5 (m,2H).

1b, R: iBu: Yield 92.6% Rf: 0.50 ($CH_2Cl_2$/MeOH/AA 9/1/0.5) $^1$H NMR ($CDCl_3$ 270 MHz): 4.35(t, 1H), 2.0(t,2H), 1.8(m, 1H), 1.0(m, 6H)

1c, R: nBu: Yield: 100% Rf: 0.48 ($CH_2Cl_2$/MeOH/AA 9/1/0.5) $^1$H NMR ($CDCl_3$ 270 MHz): 4.3(t, 1H), 2.1–1.8 (m,2H), 1.5 (m, 4H), 0.9 (t,3H).

Step 2—Synthesis of (2S)-2-Acetylsulfanyl alkyl carboxylic acids (2)

Compound 1 (0.165 mol) solubilised in 165 mL NaOH 1N (1 eq) is cooled at 0° C. Potassium thioacetate (22.65 g, 0.198 mol, 1.2 eq) in 60 mL $H_2O$ is added dropwise and the reaction mixture is stirred for 16 h at room temperature. The preparation is acidified by addition of HCl 1N (pH 1–2) then extracted with AcOEt three times. The organic layers are washed with water, NaCl sat., dried over $Na_2SO_4$, and concentrated under reduced pressure yielded compound 2 as orange oil used without further purification.

2a, R: $PhCH_2$: Yield 96.0% Rf: 0.43 (Cyclohexane/AcOEt/AA 5/5/0.1) HPLC Kromasil C18 5µ100A, 250×4.6 mm, $CH_3CN$—$H_2O$ (0.05% TFA) 40-60 $R_t$=8.9 min $^1$H NMR ($CDCl_3$ 270 MHz): 7.3(m, 5H), 4.3(t, 1H), 3.1–3.5 (m,2H), 2.2(s, 3H).

2b, R: iBu: Yield 91.0% $^1$ H NMR ($CDCl_3$ 270 MHz): 4.2(t, 1H), 2.4(s,3H), 1.9–1.5(m, 4H), 0.9(m, 6H)

2c, R: nBu: Yield: 94.5% $^1$H NMR ($CDCl_3$ 270 MHz): 4.1(t, 1H), 2.3(s, 3H), 1.9(m,1H), 1.65(m,1H), 1.3(m, 4H), 0.9 (t,3H).

Step 3—Synthesis of N-[(2S)-2-acetylsulfanyl alkanoyl]-(S)-glutamine tert-butyl ester (3)

Compound 2 (2.607 mmol), (S)-Glutamine tert-butyl ester hydrochloride (1.2 eq, 746 mg), EDCI (1.2 eq, 929 mg), HOBt (1.2 eq, 479 mg), $Et_3N$ (1.2 eq, 438 µL) are stirred overnight in 10 mL $THF/CHCl_3$. The reaction mixture is concentrated under reduced pressure and diluted in $H_2O$/AcOEt. The organic layer is washed with $NaHCO_3$ sat. (2×), citric acid 10% (2×), NaCl sat., dried over $Na_2SO_4$, and concentrated.

The crude product is purified by HPLC Kromasil C18 5μ100A, 250×20 mm (CH$_3$CN/H$_2$O 0.05% TFA 40–60) yielded compound 3 as a solid.

3a, R: PhCH$_2$: Yield 32.4%, wt: 343 mg. HPLC Kromasil C18 5μ100A, 250×4.6 mm, CH$_3$CN—H$_2$O (0.05% TFA) 50-50 R$_t$=7.88 min $^1$H NMR (CDCl$_3$ 270 MHz): 7.3–7.2(m, 5H), 4.4(m, 1H), 4.3(t, 1H), 3.2 (dd,1H), 2.8 (dd,1H), 2.2(s, 3H), 2.1(m,2H), 1.8(m,2H), 1.4(s, 9H).

3b, R: iBu: Yield 74.3%, wt: 352 mg. HPLC Kromasil C18 5μ100A, 250×4.6 mm, CH$_3$CN—H$_2$O (0.05% TFA) 50-50 R$_t$=6.48 min $^1$H NMR (CDCl$_3$ 270 MHz): 6.8(d, 1H), 4.4(m, 1H), 4.15(t, 1H), 2.4(s,3H), 2.3–1.5(m, 7H), 1.4(s, 9H), 0.9(m, 6H)

3c, R: nBu: Yield: 80.7%, wt: 307 mg. HPLC Kromasil C18 5μ100A, 250×4.6 mm, CH$_3$CN—H$_2$O (0.05% TFA) 60-40 R$_t$=6.75 min $^1$H NMR (CDCl$_3$ 270 MHz): 6.8(d, 1H), 4.4(m, 1H), 4.1(t, 1H), 2.4(s, 3H), 2.2–1.5(m, 10H), 1.4(s, 9H), 0.9 (t,3H).

Step 4—Synthesis of N-[(2S)-2-acetylsulfanyl alkanoyl]-(S)-glutamine (4)

Compound 3 (0.58 mmol) is solubilized in 3 mL CH$_2$Cl$_2$ and 3 mL TFA are added at 0° C. The reaction mixture is stirred for 3 h at room temperature. The solvent and excess reagent are eliminated under reduced pressure. The crude product is coevaporated 2 times with cyclohexane yielded compound 4 as oil used without further purification.

4a, R: PhCH$_2$: Yield 100%, wt: 206 mg. HPLC Kromasil C18 5μ100A, 250×4.6 mm, CH$_3$CN—H$_2$O (0.05% TFA) 30-70 R$_t$=8.67 min $^1$H NMR (DMSO+TFA 270 MHz): 8.5 (d, 1H), 7.2(m, 5H), 4.4(t, 1H), 4.05(m, 1H), 3.2 (dd,1H), 2.8 (dd,1H), 2.2(s, 3H), 2.1(t,2H), 1.9(m,1H), 1.8(m, 1H).

4b, R: iBu: Yield 100%, wt: 299 mg. HPLC Kromasil C18 5μ100A, 250×4.6 mm, CH$_3$CN—H$_2$O (0.05% TFA) 30-70 R$_t$=6.36 min $^1$H NMR (DMSO+TFA 270 MHz): 8.5(d, 1H), 4.3–4.0(m, 2H), 2.4(s,3H), 2.1(m, 2H)1.9(m, 1H), 1.7(m, 2H), 1.5(m, 1H), 1.3(m, 1H), 0.9(d, 3H), 0.8(d,3H)

4c, R: nBu: Yield: 100%, wt: 261 mg. HPLC Kromasil C18 5μ100A, 250×4.6 mm, CH$_3$CN—H$_2$O (0.05% TFA) 30-70 R$_t$=6.75 min $^1$H NMR (DMSO+TFA 270 MHz): 8.5(d, 1H), 4.1(m, 2H), 2.4(s, 3H), 2.1(t,2H), 1.9(m, 1H), 1.7(m, 1H), 1.6(m, 1H), 1.2(m, 3H), 0.9 (t,3H).

Step 5—Synthesis of N-[(2S)-2-mercapto alkanoyl]-(S)-glutamine (5)

Compound 4 (0.38 mmol) is solubilized under argon in 2 mL degassed MeOH and 1.16 mL degassed NaOH (3 eq) are added. The reaction mixture is stirred for 2 h at room temperature. HCl 1N is added to obtain pH=1 and the solvent is eliminated under reduced pressure. The product is extracted with AcOEt. After evaporation the product is solubilized in water and lyophilised to give 5 as a white hygroscopic solid.

5a, R: PhCH$_2$: Yield 76.5%, wt: 91 mg. HPLC Kromasil C18 5μ100A, 250×4.6 mm, CH$_3$CN—H$_2$O (0.05% TFA) 30-70 R$_t$=6.65 min SM-ES(+): [M+Na]$^+$=333 $^1$H NMR (DMSO+TFA 270 MHz): 8.5 (d, 1H), 7.2(m, 5H), 4.1(m, 1H), 3.6(q, 1H), 3.1 (dd,1H), 2.7 (dd,1H), 2.1(t, 2H), 1.9 (m,1H), 1.8(m, 1H).

5b, R: iBu: Yield 51.3%, wt: 133 mg. SM-ES(–): [M–H]$^-$= 275 HPLC Kromasil C18 5μ100A, 250×4.6 mm, CH$_3$CN—H$_2$O (0.05% TFA) 30-70 R$_t$=5.36 min $^1$H NMR (DMSO+TFA 270 MHz): 8.3(d, 1H), 4.1(m, 1H), 3.4(m, 1H), 2.1(m, 2H), 2.0–1.3(m, 5H), 0.9(d, 3H), 0.8(d,3H)

5c, R: nBu: Yield: 74.3%, 168 mg. HPLC Kromasil C18 5μ100A, 250×4.6 mm, CH$_3$CN—H$_2$O (0.05% TFA) 30-70 R$_t$=5.89 min SM-ES(+): [M+Na]$^+$=299 $^1$H NMR (DMSO+ TFA 270 MHz): 8.2(d, 1H), 4.2(m, 1H), 3.2 (q, 1H), 2.1(t,2H), 1.9(m, 1H), 1.7(m, 1H), 1.6(m, 1H), 1.2(m, 3H), 0.8 (t,3H).

SYNTHESIS EXAMPLE 2

This synthesis is described with reference to Scheme 2 of FIG. 2:

Synthesis of the Phosphinic Inhibitors

Step 1—Synthesis of Alkyl phosphinic acids (6)

The synthesis is based on the method of Boyd, E. A.; Regan, A. C.; *Tetrahedron Letters*, 1994, 24, 4223. In a 100 mL flask equipped with a septum and a condenser, 4.2 g (51.85 mol) ammonium phosphinate and HMDS (8.57 g, 53.08 mmol, 1.02 eq) are heated under N$_2$ at 100–110° C. for 2 h. The reaction mixture is cooled at 0° C. and 50 mL dried CH$_2$Cl$_2$ is added followed by the addition of the bromide derivative (53.08 mmol, 1.02 eq). The mixture is stirred overnight at room temperature.

The precipitate is filtered and the filtrate concentrated under reduced pressure. The crude product is dissolved in CH$_2$Cl$_2$/MeOH. The precipitate is removed and the crude product is eluted on silica gel (CH$_2$Cl$_2$/MeOH/AA 9/1/0.4) yielding compound 6.

6a, R: PhCH$_2$: Yield 43.3%, wt: 3.50 g. Rf: 0.21 (CH$_2$Cl$_2$/ MeOH/AA 9/1/0.4) $^1$H NMR (DMSO+TFA 270 MHz): 7.2(m, 5H), 6.9(d, 1H), 3.1(dd, 2H)

6b, R: iBu: Yield 32.1%, wt: 2.86 g. $^1$H NMR (DMSO+ TFA 270 MHz): 6.9(d, 1H), 3.6(m, 2H), 1.5(m, 1H), 0.9(m, 6H)

6c, R: nBu: Yield: 56.9%, wt: 3.60 g. $^1$H NMR (DMSO+ TFA 270 MHz): 6.9(d, 1H), 1.6(m, 2H), 1.3(m, 4H), 0.8(t, 3H)

Step 2—Synthesis of 2-(Benzyl-hydroxy-phosphi-noylmethyl)-4-(trityl-carbamoyl)-butyric ethyl ester (7a)

This synthesis is based on the method of Boyd, E. A.; Regan, A. C.; *Tetrahedron Letters*, 1994, 24, 4223. In a 25 mL flask equipped with a septum and a condenser, compound 6a (156 mg, 1 mmol) and HMDS (218 μL, 1.02 eq) are warmed up under N$_2$ at 100–110° C. for 2 h. The reaction mixture is cooled at 0° C. and compound 14 (426 mg, 1.03 mmol) in 5 mL dried CH$_2$Cl$_2$ is added. The mixture is heated overnight at 60° C.

The reaction mixture is concentrated under reduced pressure. The crude product is purified by HPLC Kromasil C18 5μ100A, 250×20 mm (CH$_3$CN/H$_2$O 0.05% TFA 60-40) yielded 234 mg compound 7a as a white solid. Yield 41.1%.

HPLC Kromasil C18 5μ100A, 250×4.6 mm, CH$_3$CN—H$_2$O (0.05% TFA) 70-30 R$_t$=5.99 min $^1$H NMR (DMSO+ TFA 270 MHz): 8.5 (s, 1H), 7.2(m, 20H), 4.1(q, 2H), 3.0(d, 2H), 2.6(m, 1H), 2.3(t, 2H), 2.0–1.6 (m, 4H), 1.1(t, 3H)

Synthesis of 2-(Alkyl-hydroxy-phosphinoylmethyl)-4-(trityl-carbamoyl)-butyric ethyl ester (7b–c)

Compound 6b or 6c (3.27 mmol) is solubilized in 3 mL CH$_3$CN. Compound 14 (1.35 g, 3.27 mmol) and BSA (4.06 mL, 5 eq) are added and the reaction mixture is stirred 72 h at room temperature under $N_2$. The reaction mixture is concentrated under reduced pressure. The crude product is purified by HPLC Kromasil C18 5μ100A, 250×20 mm ($CH_3CN/H_2O$ 0.05% TFA 60-40).

7b, R: iBu: Yield 5.3%, wt: 92 mg, white solid. HPLC Kromasil C18 5μ100A, 250×4.6 mm, $CH_3CN—H_2O$ (0.05% TFA) 70-30 $R_t$=5.57 min $^1$H NMR (DMSO+TFA 270 MHz): 8.6 (s, 1H), 7.2(m, 15H), 4.0(q, 2H), 2.6(m, 1H), 2.2(t, 2H), 1.9 (m, 2H), 1.7(m, 3H), 1.5 (m, 2H), 1.1(t, 3H), 0.9(d, 6H)

7c, R: nBu: Yield: 8.9%, wt: 155 mg, white solid. HPLC Kromasil C18 5μ100A, 250×4.6 mm, $CH_3CN—H_2O$ (0.05% TFA) 60-40 $R_t$=10.29 min $^1$H NMR (DMSO+TFA 270 MHz): 7.2(m, 15H), 6.8(s, 1H), 4.1(q, 2H), 2.7(m, 1H), 2.4–1.4(m, 12H), 1.2(t, 3H), 0.9(d, 3H)

Step 3—Synthesis of 2-(Alkyl-hydroxy-phosphinoylmethyl)-4-(trityl-carbamoyl)-butyric acid (8)

Compound 7 (0.41 mmol) is solubilized in 2 mL EtOH and 2 mL LiOH 1N(5 eq) are added. The reaction mixture is stirred for 2 h at room temperature. HCl 1N is added to obtain pH=1 and EtOH is removed under reduced pressure. The product is extracted by AcOEt. The organic layers are washed with NaCl sat., dried over $Na_2SO_4$ yielding compound 8 as oils.

8a, R: $PhCH_2$: Yield 95.0%, wt: 211 mg. HPLC Kromasil C18 5μ100A, 250×4.6 mm, $CH_3CN—H_2O$ (0.05% TFA) 40-60 $R_t$=7.70 min $^1$H NMR (DMSO+TFA 270 MHz): 8.5 (s, 1H), 7.2(m, 20H), 3.0(dd, 2H), 2.5(m, 1H), 2.3–1.6 (m, 6H)

8b, R: iBu: Yield 97.6%, wt: 81 mg. HPLC Kromasil C18 5μ100A, 250×4.6 mm, $CH_3CN—H_2O$ (0.05% TFA) 60-40 $R_t$=5.46 min $^1$H NMR (DMSO+TFA 270 MHz): 8.6 (s, 1H), 7.2(m, 15H), 2.6(m, 1H), 2.2(m, 2H), 1.9 (m, 2H), 1.7(m, 3H), 1.5(m, 2H), 0.9(d, 6H)

8c, R: nBu: Yield: 69.2%, wt: 101 mg. HPLC Kromasil C18 5μ100A, 250×4.6 mm, $CH_3CN—H_2O$ (0.05% TFA) 70-30 $R_t$=3.92 min $^1$H NMR (DMSO+TFA 270 MHz): 8.6(s, 1H), 7.2(m, 15H), 2.7(m, 1H), 2.0–1.0(m, 12H), 0.8(d, 3H)

Step 4—Synthesis of 2-(Alkyl-hydroxy-phosphinoylmethyl)-4-carbamoyl-butyric acid (9)

Compound 8 (0.197 mmol) is solubilized in 4 mL TFA in presence of 90 μL $iPr_3SiH$. The reaction mixture is stirred 2 h at room temperature. Excess TFA is removed under reduced pressure and the reaction mixture is co-evaporated with cyclohexane (2×). The crude product is purified by HPLC Kromasil C18 5μ100A, 250×20 mm ($CH_3CN/H_2O$ 0.05% TFA 30-70) yielding compound 9.

9a, R: $PhCH_2$: Yield 88.1%, wt: 52 mg, oily product. SM-ES(+): [M+H]$^+$=300 HPLC Kromasil C18 5μ100A, 250×4.6 mm, $CH_3CN—H_2O$ (0.05% TFA) 50-50 $R_t$=2.34 min $^1$H NMR (DMSO+TFA 270 MHz): 7.2(m, 5H), 3.0(d, 2H), 2.5(m, 1H), 2.0–1.6 (m, 6H)

9b, R: iBu: Yield 71.5%, wt: 30 mg, oily product. SM-ES (−): [M−H]$^-$=264 HPLC Kromasil C18 5μ100A, 250×4.6 mm, $CH_3CN—H_2O$ (0.05% TFA) 60-40 $R_t$=2.36 min $^1$H NMR (DMSO+TFA 270 MHz): 2.6(m, 1H), 2.0–1.5(m, 9H), 0.9(d, 6H)

9c, R: nBu: Yield: 98.0%, wt: 51 mg, oily product. SM-ES(−): [M−H]$^-$=264 HPLC Kromasil C18 5μ100A, 250×4.6 mm, $CH_3CN—H_2O$ (0.05% TFA) 70-30 $R_t$=3.92 min $^1$H NMR (DMSO+TFA 270 MHz): 2.5(m, 1H), 2.1–1.1 (m, 12H), 0.8(d, 3H).

SYNTHESIS EXAMPLE 3

Figure 3:
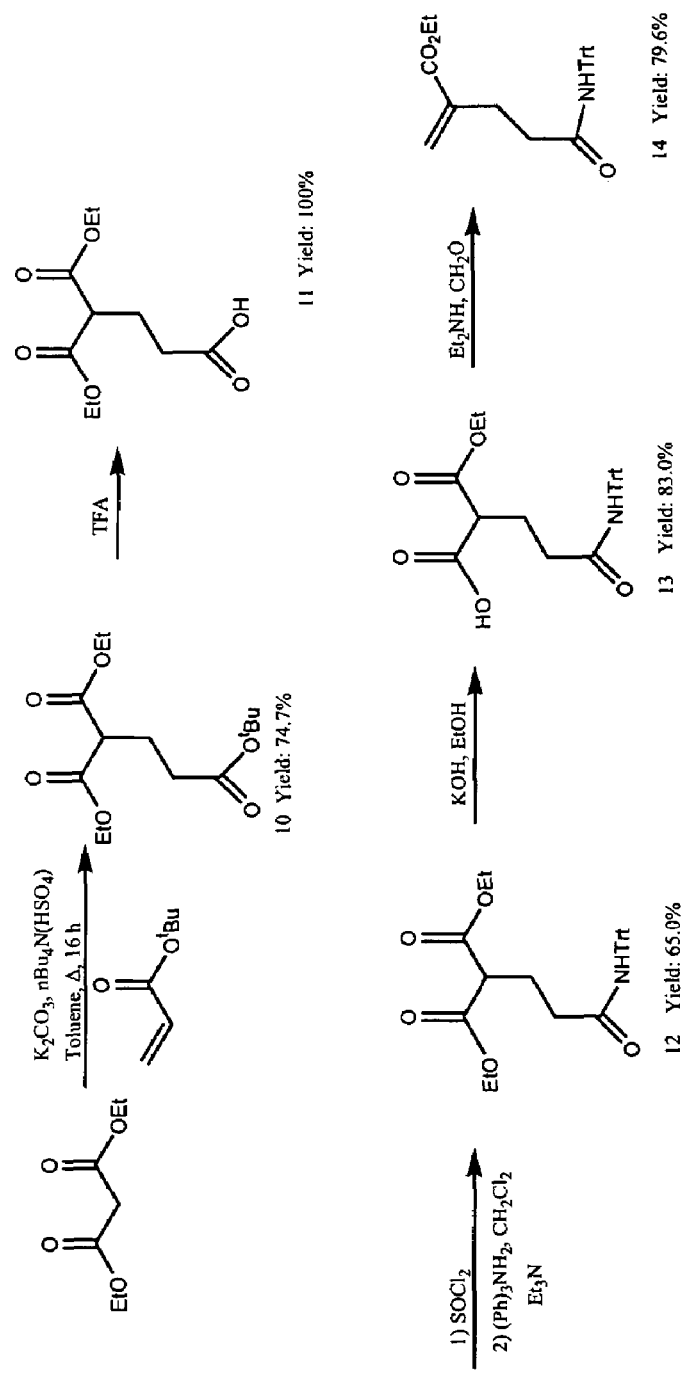

This synthesis is described with reference to Scheme 3 of FIG. 3.

Synthesis of the Ethyl 2 [2-(N-trityl)carboxamido ethyl)]acrylate

Step 1—Synthesis of Diethyl 2-(2-tert-butyloxycarbonyl ethyl)malonate (10)

In a method based on Prabhu, K. R.; Pillarsetty, N.; Gali, H.; Katti, K. V.; *J. Am. Chem. Soc.*, 2000, 122, 1554, a mixture of diethylmalonate (11.12 g, 10.55 mL, 69.46 mmol), tert-Butylacrylate (10.17 mL, 69.46 mmol, 1 eq), $K_2CO_3$ (9.60 g, 1 eq), $nBu_4NHSO_4$ (258 mg 0.01 eq) in 40 mL toluene are heated under reflux during 16 h. The reaction mixture is filtered, concentrated under vacuum yielded 19.6 g compound 10 as oil used without further purification.

Yield: 98.0% HPLC Kromasil C18 5μ100A, 250×4.6 mm, $CH_3CN—H_2O$ (0.05% TFA) 70-30 $R_t$=8.72 min $^1$H NMR ($CDCl_3$ 270 MHz): 4.1 (q, 4H), 3.3 (t, 1H), 2.2 (m, 2H), 2.05 (m, 2H), 1.3 (s, 9H), 1.1 (m, 6H).

Step 2—Synthesis of Diethyl 2-(2-carboxyethyl)malonate (11)

To a solution of compound 10 (19.6 g, 68.05 mmol), in 400 mL $CH_2Cl_2$ is added 400 mL of TFA. The mixture is stirred under during 48 h at room temperature. The reaction mixture is concentrated under vacuum, coevaporated two times with cyclohexane to eliminate excess TFA yielded 15.8 g compound 11 as oil used without further purification.

Yield: 100.0% $^1$H NMR ($CDCl_3$ 270 MHz): 8.7(s, 1H), 4.2 (q, 4H), 3.4 (t, 1H), 2.5 (m, 2H), 2.1 (m 2H), 1.2 (m,6H).

Step 3—Synthesis of Diethyl 2-(2-N-tritylcarboxamidoethyl)malonate (12)

In a method based on Haynes, R. K.; Starling, S. M.; Vonwiller, S. C.; *J. Org. Chem.*, 1995, 60, 4690, compound 11 (15.79 g, 68.10 mmol) in 12 mL thionyl chloride is heated under reflux during 1 h. The reaction mixture is concentrated under vacuum, dissolved in 20 mL $CH_2Cl_2$, then a solution of trityl amine (28.3 g 88.52 mmol) and $Et_3N$ in 20 mL $CH_2Cl_2$ is added dropwise. The reaction mixture is stirred for 48 h at room temperature.

The reaction is stopped by addition of saturated solution of $K_2CO_3$ and the desired product extracted by $Et_2O$.

The organic layer is washed with $K_2CO_3$ sat., HCl 2M, dried over $Na_2SO_4$, and concentrated under reduced pressure. The crude product is eluted on silica gel (elution CHex/AcOEt 6/4) yielded 20.9 g of the desired compound 12 as a white solid.

Yield: 65.0% Mp: 102–104° C. TLC (CHex/AcOEt 6/4) Rf:0.56 HPLC Kromasil C18 5μ100A, 250×4.6 mm, $CH_3CN—H_2O$ (0.05% TFA) 70-30 $R_t$=12.45 min $^1$H NMR ($CDCl_3$ 270 MHz): 7.4–7.1(m, 15H), 6.6(s, 1H), 4.15 (q, 4H), 3.4 (t, 1H), 2.35 (t, 2H), 2.1 (q, 2H), 1.3 (t,6H).

Step 4—Synthesis of Monoethyl 2-(2-N-tritylcarboxamidoethyl)malonate (13)

To a solution of compound 12 (20.93 g, 44.41 mmol) in 80 mL EtOH at 0° C. is added KOH (2.53 g 1.025 eq) in 100 mL EtOH. The reaction mixture is stirred for 48 h at 4° C. The reaction mixture is concentrated under reduced pressure. The mixture is dissolved in water, extracted by Et$_2$O. The aqueous layer is acidified with HCl 3M. The precipitate is filtered, dried, given 16.4 g compound 13 as a white solid.

Yield: 65.0% Mp: 122–124° C. TLC (CHex/AcOEt 6/4) Rf:0.56 HPLC Kromasil C18 5μ100A, 250×4.6 mm, CH$_3$CN—H$_2$O (0.05% TFA) 70-30 R$_t$=12.45 min $^1$H NMR (CDCl$_3$ 270 MHz): 7.4–7.1(m, 15H), 6.6(s, 1H), 4.15 (q, 2H), 3.4 (t, 1H), 2.35 (t, 2H), 2.1 (q, 2H), 1.3 (t,3H).

Step 5—Synthesis of Ethyl 2[2-(N-trityl)carboxamido ethyl)]acrylate (14)

Et$_2$NH (3.80 mL, 36.85 mmol), 37% sol. Formaldehyde (4.5 mL,1.5 eq) are mixed with compound 13 (16.4 g 36.85 mmol) and stirred 48 h at room temperature. The reaction mixture is taken up with 210 mL of a mixture H$_2$O/Et$_2$O. The aqueous layer is extracted two times with Et$_2$O. The organic layers are washed with citric acid 10%, H$_2$O, NaHCO$_3$ sat., NaCl sat., dried over Na$_2$SO$_4$, and concentrated under reduced pressure yielded compound 14 (11.71 g) as a white solid.

Yield: 79.6% Mp: 120–122° C. HPLC Kromasil C18 5μ100A, 250×4.6 mm, CH$_3$CN—H$_2$O (0.05% TFA) 7030 R$_t$=11.81 min $^1$H NMR (CDCl$_3$ 270 MHz): 7.4–7.1(m, 15H), 6.6(s, 1H), 6.1 (s, 1H), 5.6 (s, 1H), 4.14 (q, 2H), 2.6 (t, 2H), 2.4 (t, 2H), 1.3 (t,3H).

SEQUENCE DATA

SEQ ID No: 1-Peptide Sequence 1

```
  1  AQENLQKIVD SLESSRAERE ELYKWFHQHP EMSMQEHETS KRIAEELEKL
     GLEPQNIGVT

61  GQVAVIKNGE GPSVAFRADF DALPITENTG LDYSADPELG MMHACGHDLH
     TTALLGAVRA

121  LVENKDLWSG TFIAVHQPGE EGGGGARHMV DDGLAEKIAA PDVCFAQHVF
     NEDPAFGYVF

181  TPGRFLTAAS NWRIHIHGEG GHGSRPHLTK DPIVVAASII TKLQTIVSRE
     VDPNEVAVVT

241  VGSIEGGKST NSIPYTVTLG VNTRASNDEL SEYVQNAIKR IVIAECQAAG
     IEQEPEFEYL

301  DSVPAVINDE DLTEQLMAQF REFFGEDQAV EIPPLSGSED YPFIPNAWGV
     PSVMWGWSGF

361  AAGSDAPGNH TDKFAPELPD ALERGTQAIL VAAAPWLMK
```

SEQ ID No: 2-Peptide 2

A-Q-E-N-L-Q-K-I-V-D-S-L-E-S-S-R-A-E-R-E-E-L-Y-K-W-F-H-Q-H-P-E-M-S-M-Q-E

SEQ ID No: 3-Peptide 3

D-L-W-S-G-T-F-I-A-V-H-Q-P-G-E-E-I-G-G-T-K

SEQ ID No: 4-Peptide 4

W-G-W-S-G-F-A-A-G-S-D-A-P-G-N

SEQ ID No: 5-Nucleotide Sequence 1

```
  1  AATCGGGTCA TGGCACAGGA AAATTTGCAA AAGATTGTAG ATAGTCTCGA
     GTCCTCCCGC

61  GCGGAACGCG AAGAACTGTA CAAGTGGTTC CACCAGCACC CGGAAATGTC
     GATGCAGGAG

121  CACGAAACCT CCAAGCGCAT CGCAGAAGAG CTAGAGAAGC TCGGCCTTGA
     GCCGCAGAAC

181  ATCGGCGTGA CCGGGCAGGT CGCGGTAATC AAGAACGGTG AAGGCCCGAG
     CGTGGCATTT

241  CGTGCGGACT TTGATGCCTT GCCGATCACC GAGAACACCG GGCTGGATTA
     CTCGGCGGAT

301  CCCGAGCTGG GCATGATGCA CGCCTGCGGC CACGATTTGC ACACCACTGC
     CCTACTCGGC
```

```
 361  GCGGTGCGCG CGCTGGTGGA GAACAAGGAC CTGTGGTCCG GCACCTTCAT
      CGCAGTCCAC

421  CAACCCGGTG AGGAAGGCGG CGGCGGGGCC CGCCACATGG TGGACGACGG
      CCTCGCGGAG

481  AAGATCGCGG CGCCGGATGT GTGTTTCGCC CAGCACGTGT TCAACGAAGA
      CCCCGCCTTT

541  GGCTACGTGT TCACCCCCGG CCGGTTTCTA ACGGCGGCGT CGAACTGGAG
      AATCCACATC

601  CACGGCGAGG GCGGACACGG TTCCCGTCCG CACCTGACCA AGGACCCGAT
      TGTGGTGGCG

661  GCCTCGATCA TTACCAAGCT GCAGACGATT GTCTCCCGCG AAGTCGATCC
      GAATGAGGTC

721  GCAGTGGTCA CCGTCGGCTC CATCGAGGGC GGCAAGTCCA CCAACTCGAT
      CCCGTACACC

781  GTCACCCTCG GCGTGAACAC CCGAGCCTCC AACGATGAGC TCTCCGAGTA
      CGTCCAGAAC

841  GCCATCAAGC GCATCGTCAT CGCGGAGTGC CAGGCTGCAG GCATCGAACA
      GGAGCCGGAA

901  TTCGAGTACC TGGACTCAGT CCCGGCCGTG ATCAACGACG AGGATCTCAC
      CGAACAGCTC

961  ATGGCGCAGT TCCGGGAGTT CTTCGGCGAG GACCAGGCGG TAGAGATTCC
      GCCCCTGTCC

1021  GGCAGCGAGG ACTACCCCTT CATTCCGAAC GCCTGGGGCG TGCCGAGTGT
      GATGTGGGGA

1081  TGGTCCGGCT TCGCCGCAGG TTCTGACGCA CCGGGCAATC ACACCGACAA
      GTTCGCCCCC

1141  GAGCTTCCAG ATGCCCTCGA ACGCGGCACC CAGGCCATTC TGGTGGCCGC
      CGCGCCCTGG

1201  TTGATGAAGT GA

SEQ ID No: 6-Nucleotide Sequence 2

1  GGGCAGCCGG CTCACGTGGC GTGAGCGAGC GAGACCTTCG GTCGATTACC
      GCACCGAAAG

61  GAACCCCTGT GAGCGAAGCT CTCCGCGAAG AACAGCGCCT GCTCGAGCGC
      TTCATGTGGC

121  TTTCGACCAT TGCCTCCATC TTTGCCATTG CGCTGAAGCT GTACGCGGCG
      TGGGTGACGG

181  GCTCGGTCGG CTTTTTCTCC GACGCGATCG AGTCCTTTGC CAACCTGGCC
      GCTGCGGTGG

241  TGGGGCTTTG GGCGCTGAAG CTCTCGGCCA AACCGGCCGA TGCCAACCAC
      AATTTCGGCC

301  ATGCCAAGGC GGAATACTTC GCGGCGCAGG TGGAAGGCAC GATGATTCTG
      GTGGCCTCCG

361  TGGTCATCAT CGTCACCGCC GTGCAGCGCA TCATCGACCC GGCTCCGCTT
      AACCAGCTCG

421  GGATCGGCCT GGTTTTCTCC GTTGTTGCCA CCGTGATCAA CCTCGGCGTC
      GGCGTCGCGC

481  TGGTGCGGGC GGGTCGCACC CACCGCTCCA GCACACTCGA GGCCGATGGA
      AAGCATTTGC

541  TTACCGACGT CTGaACCACC GTGGGAGTCA TCGCCGGCAT GGCGTTGGTG
      TGGCTGACGG
```

-continued

SEQUENCE DATA

601 GGTGGAACGT CTTGGACCCC ATCGTGGCGT TGATTGTCGG TGCCAACATC CTCTTCACGG

661 GATACCACTG TTGCGCCAGG CGATGATGGG GCTGCTCTCC GAGGCGCTGC CGAGAGACGA

721 GGTCGAGACC GTGCAGGGGT TCTTGGACGG GTTCGCGGCA GAGCACGGCG TGGCGTTCAC

781 TTCGCTGCGC ACCTCGGCGT TTGGCCGCGA CCGCCTCATC AACGTCGTGA TGCAGGTTCC

841 CGGCGAATGG TCTGTGGAGG CCTCGCACGA GTACGCGGAC CAGGTCGAGG TGGGCATCGC

901 TACCGCGCTG GGGCACGCCG AAACCATCGT GCACATCGAA CCGCTTGGAC ATCACACCAA

961 AACAGGCCCC ATGGCGGTGT AGTAACCGCC GTAGAATCGG GTC

SEQ ID No: 7-Nucleotide Sequence 3

AAG UGG UUC CAC CAG CA

SEQ ID No: 8-Nucleotide Sequence 4

TCY TCD CCN GGC TGG TG
(Y = C/T; D = A/G/T; N = A/C/G/T)

SEQ ID No: 9-Nucleotide Sequence 5

TCR TTN GGR TCV ACY TC
(R = A/G; V = A/C/G; Y = C/T; N = A/C/G/T)

SEQ ID No: 10-Nucleotide Sequence 6

CTT CAC CGT TCT TGA TTA CCG GGA CCT

SEQ ID No: 11-Nucleotide Sequence 7

CTC TAG CTC TTC TGC GAT GCG CTT GGA

SEQ ID No: 12-Nucleotide Sequence 8

CCG CAC CTG ACC AAG GAC CCG ATT GTG

SEQ ID No: 13-Nucleotide Sequence 9

CCT CGA TCA TTA CCA AGC TGC AGA CGA

SEQ ID No: 14-Nucleotide Sequence 10

CAT GCC ATG GCA CAG GAA AAT TTG CAA

SEQ ID No: 15-Nucleotide Sequence 11

CCC AAG CTT TCA CTT CAT CAA CCA GGG CG

---

The invention claimed is:

1. An isolated $N_\alpha$-acyl-glutamine-aminoacylase comprising an amino acid sequence, which has a sequence identity of at least 95% to the amino acid sequence set forth in SEQ ID NO: 1.

2. An isolated enzyme comprising the amino acid sequence set forth in SEQ ID NO: 1.

3. An isolated enzyme encoded for by the nucleic acid comprising a the nucleotide sequence set forth in SEQ ID NO: 5.

4. A method of screening compounds for inhibitor activity of an enzyme as defined in claim 1 comprising the steps of I) incubating the enzyme of claim 1 or cell extract containing said enzyme with its substrate and a compound with potential inhibitory properties, and II) measuring release of malodorous 3-hydroxy-3-methyl-hexanoic acid or 3-methyl-3-hexanoic acid compounds and/or free L-glutamine.

* * * * *

SEQUENCE LISTING

<160> NUMBER OF SEQ ID NOS: 15

<210> SEQ ID NO 1
<211> LENGTH: 399
<212> TYPE: PRT
<213> ORGANISM: Corynebacterium striatum

<400> SEQUENCE: 1

Ala Gln Glu Asn Leu Gln Lys Ile Val Asp Ser Leu Glu Ser Ser Arg

```
              1               5              10              15

Ala Glu Arg Glu Leu Tyr Lys Trp Phe His Gln His Pro Glu Met
                    20                  25                  30

Ser Met Gln Glu His Glu Thr Ser Lys Arg Ile Ala Glu Glu Leu Glu
                    35                  40                  45

Lys Leu Gly Leu Glu Pro Gln Asn Ile Gly Val Thr Gly Gln Val Ala
                    50                  55                  60

Val Ile Lys Asn Gly Glu Gly Pro Ser Val Ala Phe Arg Ala Asp Phe
   65                   70                  75                  80

Asp Ala Leu Pro Ile Thr Glu Asn Thr Gly Leu Asp Tyr Ser Ala Asp
                    85                  90                  95

Pro Glu Leu Gly Met Met His Ala Cys Gly His Asp Leu His Thr Thr
                    100                 105                 110

Ala Leu Leu Gly Ala Val Arg Ala Leu Val Glu Asn Lys Asp Leu Trp
                    115                 120                 125

Ser Gly Thr Phe Ile Ala Val His Gln Pro Gly Glu Glu Gly Gly Gly
                    130                 135                 140

Gly Ala Arg His Met Val Asp Asp Gly Leu Ala Glu Lys Ile Ala Ala
   145                  150                 155                 160

Pro Asp Val Cys Phe Ala Gln His Val Phe Asn Glu Asp Pro Ala Phe
                    165                 170                 175

Gly Tyr Val Phe Thr Pro Gly Arg Phe Leu Thr Ala Ala Ser Asn Trp
                    180                 185                 190

Arg Ile His Ile His Gly Glu Gly Gly His Gly Ser Arg Pro His Leu
                    195                 200                 205

Thr Lys Asp Pro Ile Val Val Ala Ala Ser Ile Ile Thr Lys Leu Gln
                    210                 215                 220

Thr Ile Val Ser Arg Glu Val Asp Pro Asn Glu Val Ala Val Val Thr
   225                  230                 235                 240

Val Gly Ser Ile Glu Gly Gly Lys Ser Thr Asn Ser Ile Pro Tyr Thr
                    245                 250                 255

Val Thr Leu Gly Val Asn Thr Arg Ala Ser Asn Asp Glu Leu Ser Glu
                    260                 265                 270

Tyr Val Gln Asn Ala Ile Lys Arg Ile Val Ile Ala Glu Cys Gln Ala
                    275                 280                 285

Ala Gly Ile Glu Gln Glu Pro Glu Phe Glu Tyr Leu Asp Ser Val Pro
                    290                 295                 300

Ala Val Ile Asn Asp Glu Asp Leu Thr Glu Gln Leu Met Ala Gln Phe
   305                  310                 315                 320

Arg Glu Phe Phe Gly Glu Asp Gln Ala Val Glu Ile Pro Pro Leu Ser
                    325                 330                 335

Gly Ser Glu Asp Tyr Pro Phe Ile Pro Asn Ala Trp Gly Val Pro Ser
                    340                 345                 350

Val Met Trp Gly Trp Ser Gly Phe Ala Ala Gly Ser Asp Ala Pro Gly
                    355                 360                 365

Asn His Thr Asp Lys Phe Ala Pro Glu Leu Pro Asp Ala Leu Glu Arg
                    370                 375                 380

Gly Thr Gln Ala Ile Leu Val Ala Ala Pro Trp Leu Met Lys
   385                  390                 395

<210> SEQ ID NO 2
<211> LENGTH: 36
<212> TYPE: PRT
<213> ORGANISM: Corynebacterium striatum
```

```
<220> FEATURE:
<221> NAME/KEY: Chain
<222> LOCATION: Residues 1 to 35, SEQ ID NO: 1
<223> OTHER INFORMATION: Unmodified peptide

<400> SEQUENCE: 2

Ala Gln Glu Asn Leu Gln Lys Ile Val Asp Ser Leu Glu Ser Ser Arg
1               5                   10                  15
Ala Glu Arg Glu Glu Leu Tyr Lys Trp Phe His Gln His Pro Glu Met
            20                  25                  30
Ser Met Gln Glu
        35

<210> SEQ ID NO 3
<211> LENGTH: 21
<212> TYPE: PRT
<213> ORGANISM: Corynebacterium striatum
<220> FEATURE:
<221> NAME/KEY: Chain
<222> LOCATION: Residues 1 to 35, SEQ ID NO: 1
<223> OTHER INFORMATION: Unmodified peptide

<400> SEQUENCE: 3

Asp Leu Trp Ser Gly Thr Phe Ile Ala Val His Gln Pro Gly Glu Glu
1               5                   10                  15
Ile Gly Gly Thr Lys
            20

<210> SEQ ID NO 4
<211> LENGTH: 15
<212> TYPE: PRT
<213> ORGANISM: Corynebacterium striatum
<220> FEATURE:
<221> NAME/KEY: Chain
<222> LOCATION: Residues 355 to 369 of SEQ ID NO: 1
<223> OTHER INFORMATION: Unmodified peptide

<400> SEQUENCE: 4

Trp Gly Trp Ser Gly Phe Ala Ala Gly Ser Asp Ala Pro Gly Asn
1               5                   10                  15

<210> SEQ ID NO 5
<211> LENGTH: 1212
<212> TYPE: DNA
<213> ORGANISM: Corynebacterium striatum
<220> FEATURE:
<221> NAME/KEY: cds
<222> LOCATION: Residue 11 to 1209
<223> OTHER INFORMATION: Nucleotide sequence encoding SEQ ID NO: 1

<400> SEQUENCE: 5 aatcgggtc atg gca cag gaa aat ttg caa aag att gta gat agt ctc gag     51
          Met Ala Gln Glu Asn Leu Gln Lys Ile Val Asp Ser Leu Glu
              1               5                   10 tcc tcc cgc gcg gaa cgc gaa gaa ctg tac aag tgg ttc cac cag cac      99
Ser Ser Arg Ala Glu Arg Glu Glu Leu Tyr Lys Trp Phe His Gln His
15                  20                  25                  30 ccg gaa atg tcg atg cag gag cac gaa acc tcc aag cgc atc gca gaa     147
Pro Glu Met Ser Met Gln Glu His Glu Thr Ser Lys Arg Ile Ala Glu
                35                  40                  45 gag cta gag aag ctc ggc ctt gag ccg cag aac atc ggc gtg acc ggg     195
Glu Leu Glu Lys Leu Gly Leu Glu Pro Gln Asn Ile Gly Val Thr Gly
            50                  55                  60 cag gtc gcg gta atc aag aac ggt gaa ggc ccg agc gtg gca ttt cgt     243
Gln Val Ala Val Ile Lys Asn Gly Glu Gly Pro Ser Val Ala Phe Arg
```

```
              65                  70                  75
gcg gac ttt gat gcc ttg ccg atc acc gag aac acc ggg ctg gat tac     291
Ala Asp Phe Asp Ala Leu Pro Ile Thr Glu Asn Thr Gly Leu Asp Tyr
    80                  85                  90 tcg gcg gat ccc gag ctg ggc atg atg cac gcc tgc ggc cac gat ttg     339
Ser Ala Asp Pro Glu Leu Gly Met Met His Ala Cys Gly His Asp Leu
95                  100                 105                 110 cac acc act gcc cta ctc ggc gcg gtg cgc gcg ctg gtg gag aac aag     387
His Thr Thr Ala Leu Leu Gly Ala Val Arg Ala Leu Val Glu Asn Lys
                115                 120                 125 gac ctg tgg tcc ggc acc ttc atc gca gtc cac caa ccc ggt gag gaa     435
Asp Leu Trp Ser Gly Thr Phe Ile Ala Val His Gln Pro Gly Glu Glu
        130                 135                 140 ggc ggc ggc ggg gcc cgc cac atg gtg gac gac ggc ctc gcg gag aag     483
Gly Gly Gly Gly Ala Arg His Met Val Asp Asp Gly Leu Ala Glu Lys
            145                 150                 155 atc gcg gcg ccg gat gtg tgt ttc gcc cag cac gtg ttc aac gaa gac     531
Ile Ala Ala Pro Asp Val Cys Phe Ala Gln His Val Phe Asn Glu Asp
160                 165                 170 ccc gcc ttt ggc tac gtg ttc acc ccc ggc cgg ttt cta acg gcg gcg     579
Pro Ala Phe Gly Tyr Val Phe Thr Pro Gly Arg Phe Leu Thr Ala Ala
175                 180                 185                 190 tcg aac tgg aga atc cac atc cac ggc gag ggc gga cac ggt tcc cgt     627
Ser Asn Trp Arg Ile His Ile His Gly Glu Gly Gly His Gly Ser Arg
                195                 200                 205 ccg cac ctg acc aag gac ccg att gtg gtg gcg gcc tcg atc att acc     675
Pro His Leu Thr Lys Asp Pro Ile Val Val Ala Ala Ser Ile Ile Thr
        210                 215                 220 aag ctg cag acg att gtc tcc cgc gaa gtc gat ccg aat gag gtc gca     723
Lys Leu Gln Thr Ile Val Ser Arg Glu Val Asp Pro Asn Glu Val Ala
    225                 230                 235 gtg gtc acc gtc ggc tcc atc gag ggc ggc aag tcc acc aac tcg atc     771
Val Val Thr Val Gly Ser Ile Glu Gly Gly Lys Ser Thr Asn Ser Ile
240                 245                 250 ccg tac acc gtc acc ctc ggc gtg aac acc cga gcc tcc aac gat gag     819
Pro Tyr Thr Val Thr Leu Gly Val Asn Thr Arg Ala Ser Asn Asp Glu
255                 260                 265                 270 ctc tcc gag tac gtc cag aac gcc atc aag cgc atc gtc atc gcg gag     867
Leu Ser Glu Tyr Val Gln Asn Ala Ile Lys Arg Ile Val Ile Ala Glu
                275                 280                 285 tgc cag gct gca ggc atc gaa cag gag ccg gaa ttc gag tac ctg gac     915
Cys Gln Ala Ala Gly Ile Glu Gln Glu Pro Glu Phe Glu Tyr Leu Asp
        290                 295                 300 tca gtc ccg gcc gtg atc aac gac gag gat ctc acc gaa cag ctc atg     963
Ser Val Pro Ala Val Ile Asn Asp Glu Asp Leu Thr Glu Gln Leu Met
    305                 310                 315 gcg cag ttc cgg gag ttc ttc ggc gag gac cag gcg gta gag att ccg    1011
Ala Gln Phe Arg Glu Phe Phe Gly Glu Asp Gln Ala Val Glu Ile Pro
320                 325                 330 ccc ctg tcc ggc agc gag gac tac ccc ttc att ccg aac gcc tgg ggc    1059
Pro Leu Ser Gly Ser Glu Asp Tyr Pro Phe Ile Pro Asn Ala Trp Gly
335                 340                 345                 350 gtg ccg agt gtg atg tgg gga tgg tcc ggc ttc gcc gca ggt tct gac    1107
Val Pro Ser Val Met Trp Gly Trp Ser Gly Phe Ala Ala Gly Ser Asp
                355                 360                 365 gca ccg ggc aat cac acc gac aag ttc gcc ccc gag ctt cca gat gcc    1155
Ala Pro Gly Asn His Thr Asp Lys Phe Ala Pro Glu Leu Pro Asp Ala
        370                 375                 380 ctc gaa cgc ggc acc cag gcc att ctg gtg gcc gcc gcg ccc tgg ttg    1203
Leu Glu Arg Gly Thr Gln Ala Ile Leu Val Ala Ala Ala Pro Trp Leu
```

```
        385             390             395
atg aag tga                                                     1212
Met Lys
    400

<210> SEQ ID NO 6
<211> LENGTH: 1003
<212> TYPE: DNA
<213> ORGANISM: Corynebacterium striatum
<220> FEATURE:
<221> NAME/KEY: Untranslated region
<222> LOCATION: Residues 1 to 1003
<223> OTHER INFORMATION: PCR fragment

<400> SEQUENCE: 6
gggcagccgg ctcacgtggc gtgagcgagc gagaccttcg gtcgattacc gcaccgaaag    60
gaacccctgt gagcgaagct ctccgcgaag aacagcgcct gctcgagcgc ttcatgtggc   120
tttcgaccat tgcctccatc tttgccattg cgctgaagct gtacgcggcg tgggtgacgg   180
gctcggtcgg cttttctcc gacgcgatcg agtcctttgc caacctggcc gctgcggtgg   240
tggggctttg ggcgctgaag ctctcggcca accggccga tgccaaccac aatttcggcc    300
atgccaaggc ggaatacttc gcggcgcagg tggaaggcac gatgattctg gtggcctccg   360
tggtcatcat cgtcaccgcc gtgcagcgca tcatcgaccc ggctccgctt aaccagctcg   420
ggatcggcct ggttttctcc gttgttgcca ccgtgatcaa cctcggcgtc ggcgtcgcgc   480
tggtgcgggc gggtcgcacc caccgctcca gcacactcga ggccgatgga aagcatttgc   540
ttaccgacgt ctgaaccacc gtgggagtca tcgccggcat ggcgttggtg tggctgacgg   600
ggtggaacgt cttggacccc atcgtggcgt tgattgtcgg tgccaacatc ctcttcacgg   660
gataccactg ttgcgccagg cgatgatggg gctgctctcc gaggcgctgc cgagagacga   720
ggtcgagacc gtgcagggt tcttggacgg gttcgcggca gagcacggcg tggcgttcac    780
ttcgctgcgc acctcggcgt ttggccgcga ccgcctcatc aacgtcgtga tgcaggttcc   840
cggcgaatgg tctgtggagg cctcgcacga gtacgcggac caggtcgagg tgggcatcgc   900
taccgcgctg gggcacgccg aaaccatcgt gcacatcgaa ccgcttggac atcacaccaa   960
aacaggcccc atggcggtgt agtaaccgcc gtagaatcgg gtc                    1003

<210> SEQ ID NO 7
<211> LENGTH: 17
<212> TYPE: DNA
<213> ORGANISM: Corynebacterium striatum
<220> FEATURE:
<221> NAME/KEY: Primer
<222> LOCATION: Residue 1 to 17
<223> OTHER INFORMATION: PCR primer

<400> SEQUENCE: 7
aagugguucc accagca                                                   17

<210> SEQ ID NO 8
<211> LENGTH: 17
<212> TYPE: DNA
<213> ORGANISM: Corynebacterium striatum
<220> FEATURE:
<221> NAME/KEY: Modified_base
<222> LOCATION: Residue 3
<223> OTHER INFORMATION: Can be t, u, or c
<220> FEATURE:
<221> NAME/KEY: Modified_base
<222> LOCATION: Residue 6
<223> OTHER INFORMATION: Can be t, u, a or g
```

```
<220> FEATURE:
<221> NAME/KEY: Modified_base
<222> LOCATION: Residue 9
<223> OTHER INFORMATION: Can be a or g or c or t/u or other

<400> SEQUENCE: 8
tcytcdccng gctggtg                                                    17

<210> SEQ ID NO 9
<211> LENGTH: 17
<212> TYPE: DNA
<213> ORGANISM: Corynebacterium striatum
<220> FEATURE:
<220> FEATURE:
<221> NAME/KEY: Modified_base
<222> LOCATION: Residue 3
<223> OTHER INFORMATION: Can be a or g
<220> FEATURE:
<221> NAME/KEY: Modified_base
<222> LOCATION: Residue 6
<223> OTHER INFORMATION: Can be a or g or c or t/u or other
<220> FEATURE:
<221> NAME/KEY: Modified_base
<222> LOCATION: Residue 9
<223> OTHER INFORMATION: Can be a or g
<220> FEATURE:
<221> NAME/KEY: Modified_base
<222> LOCATION: Residue 12
<223> OTHER INFORMATION: Can be a or g or c
<220> FEATURE:
<221> NAME/KEY: Modified_base
<222> LOCATION: Residue 15
<223> OTHER INFORMATION: Can be c or t/u

<400> SEQUENCE: 9
tcrttnggrt cvacytc                                                    17

<210> SEQ ID NO 10
<211> LENGTH: 27
<212> TYPE: DNA
<213> ORGANISM: Corynebacterium striatum
<220> FEATURE:
<221> NAME/KEY: Primer
<222> LOCATION: Residue 1 to 27
<223> OTHER INFORMATION: PCR primer

<400> SEQUENCE: 10
cttcaccgtt cttgattacc gggacct                                         27

<210> SEQ ID NO 11
<211> LENGTH: 27
<212> TYPE: DNA
<213> ORGANISM: Corynebacterium striatum
<220> FEATURE:
<221> NAME/KEY: Primer
<222> LOCATION: Residue 1 to 27
<223> OTHER INFORMATION: PCR primer

<400> SEQUENCE: 11
ctctagctct tctgcgatgc gcttgga                                         27

<210> SEQ ID NO 12
<211> LENGTH: 27
<212> TYPE: DNA
<213> ORGANISM: Corynebacterium striatum
<220> FEATURE:
<221> NAME/KEY: Primer
<222> LOCATION: Residue 1 to 27
<223> OTHER INFORMATION: PCR primer

<400> SEQUENCE: 12
```

```
ccgcacctga ccaaggaccc gattgtg                                          27

<210> SEQ ID NO 13
<211> LENGTH: 27
<212> TYPE: DNA
<213> ORGANISM: Corynebacterium striatum
<220> FEATURE:
<221> NAME/KEY: Primer
<222> LOCATION: Residue 1 to 27
<223> OTHER INFORMATION: PCR primer

<400> SEQUENCE: 13
cctcgatcat taccaagctg cagacga                                          27

<210> SEQ ID NO 14
<211> LENGTH: 27
<212> TYPE: DNA
<213> ORGANISM: Corynebacterium striatum
<220> FEATURE:
<221> NAME/KEY: Primer
<222> LOCATION: Residue 1 to 27
<223> OTHER INFORMATION: PCR primer

<400> SEQUENCE: 14
catgccatgg cacaggaaaa tttgcaa                                          27

<210> SEQ ID NO 15
<211> LENGTH: 29
<212> TYPE: DNA
<213> ORGANISM: Corynebacterium striatum
<220> FEATURE:
<221> NAME/KEY: Primer
<222> LOCATION: Residue 1 to 29
<223> OTHER INFORMATION: PCR primer

<400> SEQUENCE: 15
cccaagcttt cacttcatca accagggcg                                        29
```